(12) United States Patent
Stemmer et al.

(10) Patent No.: US 6,483,011 B1
(45) Date of Patent: Nov. 19, 2002

(54) MODIFIED ADP-GLUCOSE PYROPHOSPHORYLASE FOR IMPROVEMENT AND OPTIMIZATION OF PLANT PHENOTYPES

(75) Inventors: Willem P. C. Stemmer, Los Gatos, CA (US); Venkiteswaran Subramanian, San Diego, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/721,540

(22) Filed: Nov. 22, 2000

Related U.S. Application Data

(63) Continuation of application No. 09/437,725, filed on Nov. 9, 1999, now abandoned.
(60) Provisional application No. 60/107,782, filed on Nov. 10, 1998.

(51) Int. Cl.[7] .......................... A01H 1/00; C12N 15/82; C12N 15/87; C12N 5/04; C12N 5/10; C12Q 1/68
(52) U.S. Cl. ........................ 800/284; 435/6; 435/419
(58) Field of Search ...................... 435/6, 419; 800/284

(56) References Cited

U.S. PATENT DOCUMENTS

| | | |
|---|---|---|
| 4,407,956 A | 10/1983 | Howell |
| 4,683,202 A | 7/1987 | Mullis et al. |
| 5,270,170 A | 12/1993 | Schatz et al. |
| 5,358,665 A | 10/1994 | Sienkowski et al. |
| 5,512,463 A | 4/1996 | Stemmer |
| 5,514,588 A | 5/1996 | Varadaraj |
| 5,605,793 A | 2/1997 | Stemmer |
| 5,763,239 A | 6/1998 | Short et al. |
| 5,789,228 A | 8/1998 | Lam et al. |
| 5,811,238 A | 9/1998 | Stemmer et al. |
| 5,814,473 A | 9/1998 | Warren et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minushull et al. |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |

(List continued on next page.)

FOREIGN PATENT DOCUMENTS

| | | |
|---|---|---|
| EP | 0270356 B1 | 6/1994 |
| EP | 0911396 A2 | 4/1999 |
| EP | 0911396 A3 | 5/1999 |
| EP | 0934999 A1 | 8/1999 |
| WO | WO 89/30776 | 7/1986 |
| WO | WO-91/91806 | * 12/1991 |
| WO | WO 94/24292 | 10/1994 |
| WO | WO 95/22625 | 8/1995 |
| WO | WO 96/33207 | 10/1996 |
| WO | WO 97/07205 | 2/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08529 | 2/1999 |
| WO | WO 99/10472 | 3/1999 |
| WO | WO 99/10539 | 3/1999 |

(List continued on next page.)

OTHER PUBLICATIONS

Harayama S., "Artificial evolution by DNA shuffling", Trends in Biotechnology vol. 16, pp. 76–82 (Feb. 1998).*

Barman T. E., "Enzyme Handbook", Springer–Verlag Berlin–Heidelberg, vol. 1, pp. 6–12 (1985).*

Stemmer, Willem P., "DNA shuffling by random fragmentation and reassembly: In vitro recombination for molecular evolution" *Proc. Natl. Acad. Sci.* vol. 91, pp. 10747–10751, Oct. 1994.

Crameri et al., "DNA Shuffling of a family of genes from diverse species accelerates directed evolution", *Nature* vol. 391 pp. 288–291.

Smith–White, B., et al., "Comparison of Proteins of ADP–Glucose Pyrophosphorylase from Diverse Sources" *Journal of Molecular Evolution* 1992, 34:449–464.

Greene, T., et al., "Generation of up–regulated allosteric variants of potato ADP–glucose pyrophosphorylase by reversion genetics" *Proc. Natl. Acad. Sci.* vol. 95, pp. 10322–10327, Aug. 1998.

Harayama, S., "Artificial evolution by DNA shuffling" *Trends in Biotechnology* Feb. 1998, vol. 16 pp. 76–82.

(List continued on next page.)

Primary Examiner—Kenneth R. Horlick
Assistant Examiner—Teresa Strzelecka
(74) Attorney, Agent, or Firm—Townsend and Townsend and Crew LLP

(57) ABSTRACT

The invention provides methods and compositions relating to sequence-shuffled variants of ADP-glucose pyrophosphorylase.

17 Claims, 2 Drawing Sheets

U.S. PATENT DOCUMENTS

| | | | |
|---|---|---|---|
| 5,958,672 | A | 9/1999 | Short |
| 5,958,751 | A | 9/1999 | Murphy et al. |
| 5,962,258 | A | 10/1999 | Mathur et al. |
| 5,962,283 | A | 10/1999 | Warren et al. |
| 5,965,408 | A | 10/1999 | Short |
| 5,985,646 | A | 11/1999 | Murphy et al. |

FOREIGN PATENT DOCUMENTS

| | | |
|---|---|---|
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |

OTHER PUBLICATIONS

Rudi, H., et al., "A (His)6–tagged recombinant barley (Hordeum vulgare L.) endosperm ADP–glucose pyrophosphorylase expressed in the baculovirus–insect cell system . . . " *FEBS Letters* Dec. 1997, vol. 419, No. 1 pp. 124–130.

Chang et al. (1999) Evolution of a cytokine using DNA family shuffling *Nature Biotechnology* 17: 793–797.

Christians et al. (1999) Directed evolution of thymidine kinase for AZT phosphorylation using DNA family shuffling *Nature Biotechnology* 17:259–264.

Crameri and Stemmer (1995) Combinatorial multiple cassette mutagenesis creates all the permutations of mutant and wildtype cassettes@ *Biotechniques* 18:194–195.

Crameri et al. (1996) Construction and evolution of antibody–phage libraries by DNA shuffling *Nature Medicine* 2:100–103.

Crameri et al. (1996) Improved green fluorescent protein by molecular evolution using DNA shuffling *Nature Biotechnology* 14:315–319.

Crameri et al. (1997) Molecular evolution of an arsenate detoxification pathway by DNA shuffling, *Nature Biotechnology* 15:436–438.

Falcone and Tabita (1993) *J. Bact. 175:* 5066.

Falcone et al. (1991) *J. Bact. 173:* 2099.

Falcone et al. (1998) *J. Bact. 170:* 5.

Gates et al. (1996) Affinity selective isolation of ligands from peptide libraries through display on a lac repressor 'headpiece dimer' *Journal of Molecular Biology* 255: 373–386.

Minshull and Stemmer (1999) Protein evolution by molecular breeding *Current Opinion in Chemical Biology* 3:284–290.

Ness et al. (1999) DNA Shuffling of subgenominc sequences of subtilisin *Nature Biotechnology* 17:893–896.

O'Neill et al. (1993) *The Plant Journal 3:* 729.

Patten et al. (1997) Applications of DNA Shuffling to Pharmaceuticals and Vaccines *Current Opinion in Biotechnology* 8:724–733.

Stemmer (1994) *PNAS 91:* 10747–10751.

Stemmer (1994) Rapid evolution of a protein in vitro by DNA shuffling *Nature* 370:389–391.

Stemmer (1995) Searching Sequence Space@ *Bio/Technology* 13:549–553.

Stemmer (1995) The Evolution of Molecular Computation@ *Science* 270: 1510.

Stemmer (1996) Sexual PCR and Assembly PCR In: *The Encyclopedia of Molecular Biology.* VCH Publishers, New York, pp. 447–457.

Stemmer et al., (1995) Single–step assembly of a gene and entire plasmid form large numbers of oligodeoxyribonucleotides *Gene,* 164:49–53.

Stemmer, et al., (1999) Molecular breeding of viruses for targeting and other clinical properties. Tumor Targeting 4:1–4.

Zhang et al. (1997) Directed evolution of an effective fucosidase from a galactosidase by DNA shuffling and screening *Proceedings of the National Academy of Sciences, U.S.A.* 94:4504–4509.

Altschul et al., *J. Mol. Biol.* 215:403–410 (1990).

Baker et al (1985) Plant Genetics, 201–211.

Ball et al. (1991) *Planta 185:* 17.

Byteiber, et al. (1987) Proc. Natl. Acad. Sci. USA: 5345–5349.

Daniell et al. (1998) *Nature Biotechnology 16:* 346.

de la Pena et al. [1987], Nature 325:274–276.

Dunn et al. (1988) *J. Biol. Chem. 263:* 10878.

Dunn et al. (1989) *J. Biol. Chem. 264:* 13057.

Eckert, K.A. and Kunkel, T.A. (1991) *PCR Methods and Applications 1:* 17.

Fraley et al., (1983) *Proc. Natl. Acad. Sci. USA* 80:4803.

Fromm et al. [1986] Nature 319:791–793.

Fromm et al., (1985) "Expression of Genes Transferred into Monocot and Dicot Plant Cells by Electroporation," *Proc. Natl Acad. Sci. USA* 82:5824.

Goodspeed et al. (1989) *Gene 76:*1.

Graves and Goldman, (1986) Plant Mol. Biol 7: 43–50.

Greene TW et al. (1996) *PNAS 93:* 1509–151.

Hayashimoto et al. (1990) *Plant Physiol. 93:* 857.

Henikoff & Henikoff (1989) *Proc. Natl. Acad. Sci. USA* 89:10915.

Hernalsteens et al., (1984) EMBO J. 3: 3039–41.

Hohn et al., (1982) "Molecular Biology of Plant Tumors," Academic Press, New York, pp. 549–560.

Hooykas–Van Slogteren et al., (1984) *Nature* 311:763–764.

Horsch et al., (1984) "Inheritance of Functional Foreign Genes in Plants," *Science,* 233:496–498.

Iglesias A et al. *J. Biol Chem 268:* 1081–1086.

Klee et al., (1987) *Annual Review of Plant Physiology,* 38:467–486.

Klein et al., (1987) *Nature* 327:70–73.

Mattila et al. (1991) *Nucleic Acids Res. 19:* 4967.

Needleman and Wunsch (1970) *J. Mol. Biol. 48:* 443.

Paszkowski et al., (1984) *EMBO J.* 3:2717–22.

Pearson and Lipman (1988) *Proc. Natl. Acad. Sci. (U. S. A.) 85:* 244.

Smith and Waterman (1981) *Adv. Appl Math. 2:* 482.

Steiner et al. (1977) *J. Bact. 129:* 246.

Crameri et al., (1993) "10(20)–Fold aptamer library amplification without gel purification," *Nuc. Acids Res.* 21(18):4410.

Stemmer, W.P.C. & Soong, N.W. (1999) "Molecular breeding of viruses for targeting and other clinical properties." *Tumor Targeting* 4:59–62.

Feng & Doolittle, *J. Mol. Evol.,* 35:351–360 (1987).

Higgins & Sharp, *CABOIS* 5:151–153 (1989).

Li et al. (1990) Plant Molecular Biology Report 8(4)276–291.
Lyznik et al. (1991) *BioTechniques* 10:295.
Maliga P (1993) *TIBTECH* 11: 101.
Preiss et al. (1966) *Biochemistry* 5: 1833.
Preiss J, (1996) *Biotechnology Annual Review* vol. 2, pp. 259–279.

Meyer et al., "Site–Directed Mutagenesis of a Regulatory Site of *Escherichia coli* ADP–Glucose Pyrophosphrylase: The Role of Residue 336 in Allosteric Behavior" *Archives of Biochemistry and Biophysics* vol. 353, No. 1, May 1, 1998, pp. 152–159.

* cited by examiner

US 6,483,011 B1

MODIFIED ADP-GLUCOSE PYROPHOSPHORYLASE FOR IMPROVEMENT AND OPTIMIZATION OF PLANT PHENOTYPES

CROSS REFERENCE TO RELATED APPLICATIONS

This application is a continuation of the application number 09/437,725, filed Nov. 9, 1999, now abandoned, which claims priority to the provisional parent application "MODIFIED ADP-GLUCOSE PYROPHOSPHORYLASE FOR IMPROVEMENT AND OPTIMIZATION OF PLANT PHENOTYPES" by Willem P. C. Stemmer and Venkitswaran Subramanian, U.S. Pat. No. 60/107,782, filed Nov. 10, 1998.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates to methods and compositions for generating, modifying, adapting, and optimizing polynucleotide sequences that encode proteins having ADPGPP enzyme activities which are useful for introduction into plant species, and other hosts, and related aspects.

BACKGROUND

Genetic Engineering of Plants

Genetic engineering of agricultural organisms dates back thousands of years to the dawn of agriculture. The hand of man has selected the agricultural organisms having the phenotypic traits that were deemed desirable, which desired phenotypic traits have often been taste, high yield, caloric value, ease of propagation, resistance to pests and disease, and appearance. Classical breeding methods to select for germplasm encoding desirable agricultural traits had been a standard practice of the world's farmers long before Gregor Mendel and others identified the basic rules of segregation and selection. For the most part, the fundamental process underlying the generation and selection of desired traits was the natural mutation frequency and recombination rates of the organisms, which are quite slow compared to the human lifespan and make it difficult to use conventional methods of breeding to rapidly obtain or optimize desired traits in an organism.

The very recent advent of non-classical, or "recombinant" genetic engineering techniques has provided a new means to expedite the generation of agricultural organisms having desired traits that provide an economic, ecological, nutritional, or aesthetic benefit. To date most recombinant approaches have involved transferring a novel or modified gene into the germline of an organism to effect its expression or to inhibit the expression of the endogenous homologue gene in the organism's native genome. However, the currently used recombinant techniques are generally unsuited for substantially increasing the rate at which a novel or improved phenotypic trait can be evolved. Essentially all recombinant genes in use today for agriculture are obtained from the germplasm of existing plant and microbial specimens, which have naturally evolved coordinately with constraints related to other aspects of the organism's evolution and typically are not optimized for the desired phenotype(s). The sequence diversity available is limited by the natural genetic variability within the existing specimen gene pool, although crude mutagenic approaches have been used to add to the natural variability in the gene pool.

Unfortunately, the induction of mutations to generate diversity often requires chemical mutagenesis, radiation mutagenesis, tissue culture techniques, or mutagenic genetic stocks. These methods provide means for increasing genetic variability in the desired genes, but frequently produce deleterious mutations in many other genes. These other traits may be removed, in some instances, by further genetic manipulation (e.g., backcrossing), but such work is generally both expensive and time consuming. For example, in the flower business, the properties of stem strength and length, disease resistance and maintaining quality are important, but often initially compromised in the mutagenesis process.

ADP-Glucose Pyrophosphorylase

The biosynthesis of starches in higher plants occurs in three steps, the first of which involves synthesis of ADP glucose from ATP and $\alpha$-glucose-1-phosphate, and which is catalyzed by ADP-glucose pyrophosphorylase ("ADPGPP"; EC 2.7.7.27). The second step of starch biosynthesis is transfer of a glucosyl moiety of ADP-glucose to a maltodextrin or starch to give rise to a new $\alpha$-1,4-glucosyl linkage; the reaction is catalyzed by a starch synthase, of which there are several forms present either as soluble enzymes or bound to starch particles as particulate enzymes. The third reaction is catalyzed by branching enzyme and is responsible for synthesis of $\alpha$-1,6-glucosyl linkages.

Starch synthesis in plants is tightly regulated and is tied to photosynthetic carbon fixation. Principal control of starch synthesis in plants, algae, and bacteria is at the level of ADPGPP. It has been shown that reduced ADPGPP activity in Arabidopsis leaves and potato tubers results in a reduced rate of starch synthesis. The ADPGPP enzyme in plants exists primarily as a tetramer, $S_2L_2$, composed of two different subunits of approximately 50–60 kDa each. The molecular weight of the small (S) subunit is approximately 50–55 kDa, and the S subunit is the catalytic protein having the enzymatic active site (e.g., reaction center). The molecular weight of the large (L) subunit is approximately 55–60 kDa, and the L subunit is the regulatory subunit protein. The plant enzyme is strongly activated by 3-phosphoglycerate (PGA), a product of carbon dioxide fixation; in the absence of PGA, the enzyme exhibits only about 3% of its activity. Plant ADPGPP is also strongly inhibited by inorganic phosphate (Pi). In contrast, bacterial and algal ADPGPP exist as homotetramers of 50kDa. The Algal enzyme, like its plant counterpart, is activated by PGA and inhibited by Pi, whereas the bacterial enzyme is activated by fructose-1, 6-bisphosphate (FBP) and inhibited by AMP and Pi.

In the last 10 years, the demand for starch has dramatically increased both for food and industrial uses, primarily as a result of increased demand for high fructose corn syrups and biofuel. Hence, mobilizing a greater proportion of the photosynthetic assimilates of major crops into the seeds and other sinks in the form of starch can be expected to have a major impact on agriculture in the form of increased yield of harvestable parts. Deregulating starch biosynthesis by deregulating ADPGPP (e.g., decoupling from the need for positive activation and/or negative inhibition of catalytic activity) in order to increase both the rate of accumulation and the amount of starch in sinks such as tubers (e.g., potato) and seeds (e.g., maize, wheat, rice). A mutant form of *E. coli* ADPGPP gene (Gig C16) has been introduced into potato and exhibits a significant activity in the absence of its normal activator, FGP, and is much less sensitive to feedback inhibition by AMP and Pi. Transgenic potato plants expressing this gene under the control of a tuber-specific promoter showed 25–60% more starch in tubers as compared to control non-transgenic plants.

As noted, the advent of recombinant DNA technology has provided agriculturists with additional means of modifying plant genomes. While certainly practical in some areas to date genetic engineering methods have had limited success in transferring or modifying important biosynthetic or other pathways including the ADPGPP enzyme in photosynthetic organisms and bacteria. The creation of plants and other photosynthetic organisms having improved ADPGPP biosynthetic pathways can provide increased yields of certain types of starchy foodstuffs, enhanced biomass energy sources, and may alter the types and amounts of nutrients present in certain foodstuffs, among other desirable phenotypes.

Thus, there exists a need for improved methods for producing plants and agricultural photosynthetic microbes with an improved ADPGPP enzyme. In particular, these methods should provide general means for producing novel ADPGPP enzymes, including increasing the diversity of the ADPGPP gene pool and the rate at which genetic sequences encoding one or more ADPGPP subunits having desired properties are evolved. It is particularly desirable to have methods which are suitable for rapid evolution of genetic sequences to function in one or more plant species and confer an improved ADPGPP phenotype (e.g., reduced sensitivity to inhibitors (e.g., Pi, AMP), reduced dependence on activators (e.g., PGA, FBP), improved catalytic efficiency via increasing Vmax and/or increasing the apparent affinity of substrates for the enzyme, and/or relieving a requirement for allosteric activation or inhibition by allosteric repression, as well as plants which express the novel ADPGPP genetic sequence(s).

The present invention meets these and other needs and provides such improvements and opportunities.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference, whether specifically noted as such or not.

SUMMARY OF THE INVENTION

In a broad general aspect, the present invention provides a method for the rapid evolution of one or more polynucleotide sequences encoding a ADPGPP enzyme, or one or more subunits thereof; that, when transferred into an appropriate plant cell, or photosynthetic microbial host and expressed therein, confers an enhanced metabolic phenotype to the host to increase starch formation ratio and/or rate, or to increase the accumulation or depletion of certain starches. In general, polynucleotide sequence shuffling and phenotype selection, such as detection of a parameter of ADPGPP enzyme activity, is employed recursively to generate polynucleotide sequences which encode novel proteins having desirable ADPGPP enzymatic catalytic function(s), regulatory function(s), and related enzymatic and physicochemical properties. Although the method is believed broadly applicable to evolving biosynthetic enzymes having desired properties, the invention is described principally with reference to the metabolic enzyme activities of plants and/or photosynthetic microbes and/or bacteria, defined as ADPGPP, or an isozyme thereof, including both catalytic subunit (small subunit, S; gene designation, S) and allosteric regulatory subunit (large subunit, L; gene designation, L), respectively, as appropriate for plant and algal ($S_2L_2$), as well as bacterial ($S_4$).

In one aspect, the invention provides methods of producing a recombinant cell having an elevated starch production activity. In the methods, one or more first ADGPP enzyme coding nucleic acid, or a homologue thereof, is recombined with one or more homologous first nucleic acid to produce a library of recombinant first enzyme nucleic acid homologues. This step can be repeated as desired to produce a more diverse library of recombinant first enzyme nucleic acid homologues. The libraries are selected for an activity which aids in Starch production, such as an increased or decreased catalytic rate, an altered substrate specificity, an increased ability of a cell expressing one or more members of the library to produce starch when the one or more library members is expressed in the cell, etc., thereby producing a selected library of recombinant first enzyme nucleic acid homologues. These steps are recursively repeated until one or more members of the selected library produces an elevated starch production level in a target recombinant cell when the one or more selected library member is expressed in the target cell, as compared to a starch fixation activity of the target cell when the one or more selected library member is not expressed in the target cell.

Other features and advantages of the invention will be apparent from the following description of the drawings, preferred embodiments of the invention, the examples, and the claims.

BRIEF DESCRIPTION OF THE DRAWINGS

FIG. 1A shows a diagrammatic representation of ADPGPP activity as a function of activator concentration for a parental wild-type ADPGPP (solid line), a shufflant which is partially desensitized (dotted line), and a shufflant which is fully desensitized (dashed line) to activator. FIG. 1B shows a diagrammatic representation of ADPGPP activity as a function of inhibitor concentration for a parental wild-type ADPGPP (solid line), a shufflant which is partially desensitized (dotted line), and a shufflant which is fully desensitized (dashed line) to inhibitor.

FIG. 2A shows a diagrammatic representation of ADPGPP activity as a function of substrate concentration for a parental wild-type ADPGPP (solid line), and a shufflant which is optimized for substrate usage(dashed line); Km for the wildtype Km(wt) and optimized enzyme Km(opt), and Vmax for the wildtype Vmax(wt) and optimized Vmax(opt) are shown. FIG. 2B shows a diagrammatic representation of ADPGPP activity as a function of inhibitor concentration for a parental wild-type ADPGPP (solid line), and a shufflant which is optimized for substrate usage(dashed line); Km for the wildtype Km(wt) and optimized enzyme Km(opt), and Vmax for the wildtype Vmax(wt) and optimized Vmax(opt) are shown.

DETAILED DESCRIPTION

Definitions

Figure 1:
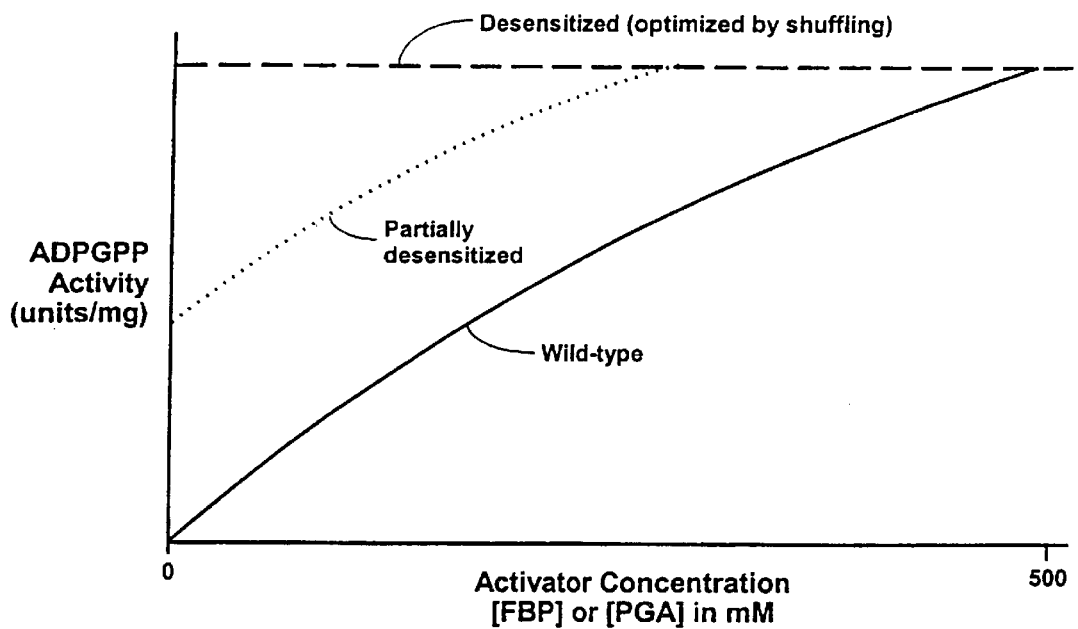
FIG. 1. Desensitization of ADPGPP to activator and inhibitor.
Figure 1:
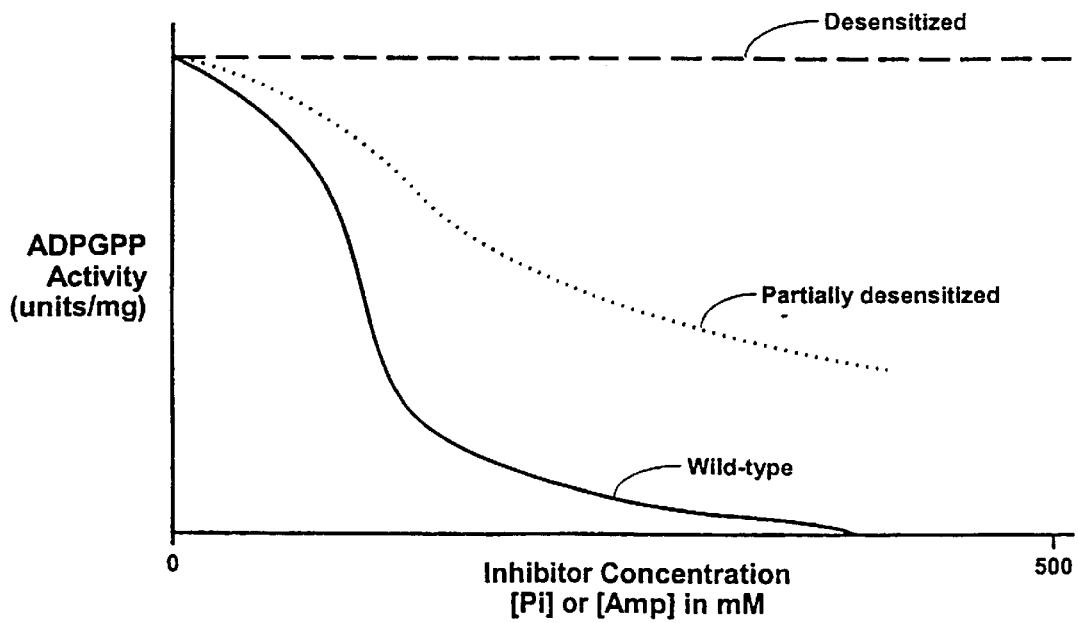
Figure 2:
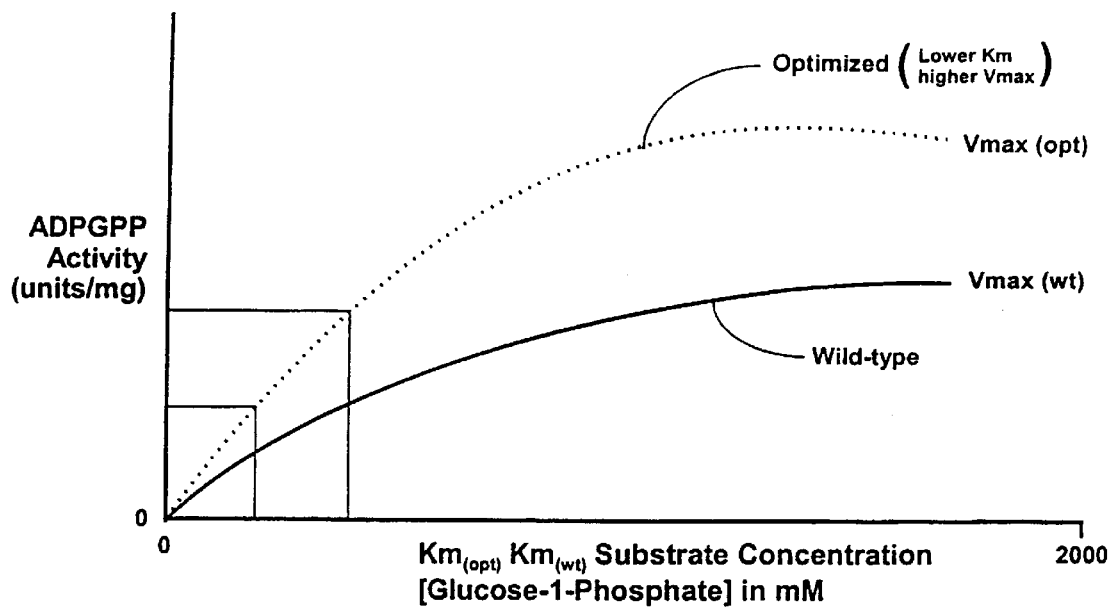
FIG. 2. Optimization by shuffling of ADPGPP for substrate usage and resistance to inhibition.
Figure 2:
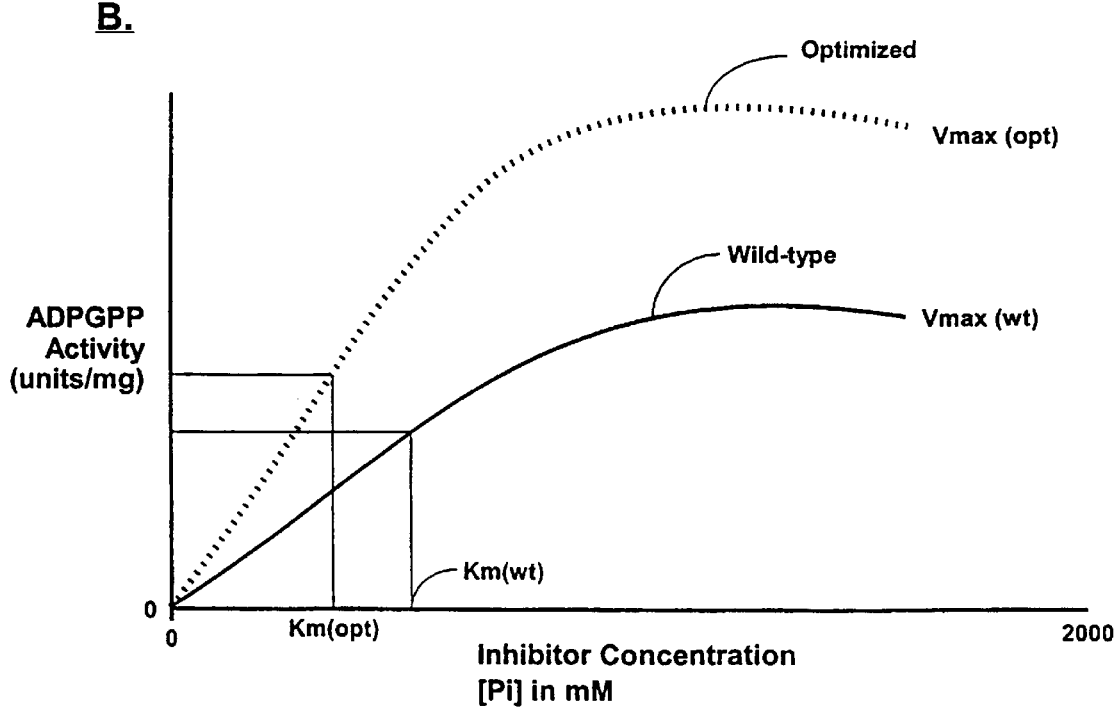

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "shuffling" is used herein to indicate recombination between substantially homologous but non-identical polynucleotide sequences; in some embodiments, DNA shuffling may involve crossover via nonhomologous recombination, such as via cre/lox and/or flp/frt systems, or by oligonucleotide or in silico shuffling, or the like, such that recombination need not require substantially homologous polynucleotide sequences. Homologous and non-homologous recombination formats can be used, and, in some embodiments, can generate molecular chimeras and/or molecular hybrids of substantially dissimilar sequences. Viral recombination systems, such as template-switching and the like can also be used to generate molecular chimeras and recombined genes, or portions thereof. A general description of shuffling is provided in commonly-assigned W098/13487 and W098/13485, both of which are incorporated herein in their entirety by reference; in case of any conflicting description of definition between any of the incorporated documents and the text of this specification, the present specification provides the principal basis for guidance and disclosure of the present invention.

The term "related polynucleotides" means that regions or areas of the polynucleotides are identical and regions or areas of the polynucleotides are heterologous.

The term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

The term "cleaving" means digesting the polynucleotide with enzymes or breaking the polynucleotide (e.g., by chemical or physical means), or generating partial length copies of a parent sequence(s) via partial PCR extension, PCR stuttering, differential fragment amplification, or other means of producing partial length copies of one or more parental sequences.

The term "population" as used herein means a collection of components such as polynucleotides, nucleic acid fragments or proteins. A "mixed population" means a collection of components which belong to the same family of nucleic acids or proteins (i.e. are related) but which differ in their sequence (i.e. are not identical) and hence in their biological activity.

The term "mutations" means changes in the sequence of a parent nucleic acid sequence (e.g., a gene or a microbial genome, transferable element, or episome) or changes in the sequence of a parent polypeptide. Such mutations may be point mutations such as transitions or transversions. The mutations may be deletions, insertions or duplications.

The term "recursive sequence recombination" as used herein refers to a method whereby a population of polynucleotide sequences are recombined with each other by any suitable recombination means (e.g., sexual PCR, homologous recombination, site-specific recombination, etc.) to generate a library of sequence-recombined species which is then screened or subjected to selection to obtain those sequence-recombined species having a desired property; the selected species are then subjected to at least one additional cycle of recombination with themselves and/or with other polynucleotide species and at subsequent selection or screening for the desired property.

The term "amplification" means that the number of copies of a nucleic acid fragment is increased.

The term "naturally-occurring" as used herein as applied to an object refers to the fact that an object can be found in nature. For example, a polypeptide or polynucleotide sequence that is present in an organism that can be isolated from a source in nature and which has not been intentionally modified by man in the laboratory-is naturally-occurring. As used herein, laboratory strains and established cultivars of plants which may have been selectively bred according to classical genetics are considered naturally-occurring. As used herein, naturally-occurring polynucleotide and polypeptide sequences are those sequences, including natural variants thereof, which can be found in a source in nature, or which are sufficiently similar to known natural sequences that a skilled artisan would recognize that the sequence could have arisen by natural mutation and recombination processes.

As used herein "predetermined" means that the cell type, non-human animal, or virus may be selected at the discretion of the practitioner on the basis of a known phenotype.

As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene which is operably linked to a polynucleotide sequence corresponding to a transcriptional regulatory sequence of an endogenous gene is generally expressed in substantially the same temporal and cell type-specific pattern as is the naturally-occurring gene.

As used herein, the terms "expression cassette" refers to a polynucleotide comprising a promoter sequence and, optionally, an enhancer and/or silencer element(s), operably linked to a structural sequence, such as a cDNA sequence or genomic DNA sequence. In some embodiments, an expression cassette may also include polyadenylation site sequences to ensure polyadenylation of transcripts. When an expression cassette is transferred into a suitable host cell, the structural sequence is transcribed from the expression cassette promoter, and a translatable message is generated, either directly or following appropriate RNA splicing. Typically, an expression cassette comprises: (1) a promoter, such as a CaMV 35S promoter, a NOS promoter or a rbcS promoter, or other suitable promoter known in the art, (2) a cloned polynucleotide sequence, such as a cDNA or genomic fragment ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, pCD and λNMT (Okayama H and Berg P (1983) *Mol. Cell. Biol.* 3: 280; Okayama H and Berg P (1985) *Mol. Cell. Biol.* 5: 1136, incorporated herein by reference). With reference to expression cassettes which are designed to function in chloroplasts, such as an expression cassette encoding a large or small subunit of ADPGPP in a higher plant, the expression cassette comprises the sequences necessary to ensure expression in chloroplasts or translocation of a nuclear-encoded form translated in the cytoplasm into the chloroplast. For embodiments wherein the ADPGPP subunits(s) are expressed in chloroplasts, typically the subunit encoding sequence is flanked by two regions of homology to the plastid genome so as to effect a homologous recombination with the chloroplastid genome; often a selectable marker gene is also present within the flanking plastid DNA sequences to facilitate selection of genetically stable transformed chloroplasts in the resultant transplastonic plant cells (see Maliga P (1993) TIBTECH 11: 101: Daniell et al. (1998) *Nature Biotechnology* 16: 346, and references cited therein).

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

As used herein, the term "transcription regulatory region" refers to a DNA sequence comprising a functional promoter and any associated transcription elements (e.g., enhancer, CCAAT box, TATA box, LRE, ethanol-inducible element, etc.) that are essential for transcription of a polynucleotide sequence that is operably linked to the transcription regulatory region.

As used herein, the term "xenogeneic" is defined in relation to a recipient genome, host cell, or organism and means that an amino acid sequence or polynucleotide sequence is not encoded by or present in, respectively, the naturally-occurring genome of the recipient genome, host cell, or organism. Xenogenic DNA sequences are foreign DNA sequences. Further, a nucleic acid sequence that has been substantially mutated (e.g., by site directed mutagenesis) is xenogeneic with respect to the genome from which the sequence was originally derived, if the mutated sequence does not naturally occur in the genome.

The term "corresponds to" is used herein to mean that a polynucleotide sequence is homologous (i.e., identical) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "5'-TATAC" corresponds to a reference sequence "5'-TATAC" and is complementary to a reference sequence "5'-GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length viral gene or virus genome. Generally, a reference sequence is at least 20 nucleotides in length, frequently at least 25 nucleotides in length, and often at least 50 nucleotides in length. Since two polynucleotides may each comprise (1) a sequence (i.e., a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which for comparative purposes in this manner does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence (e.g., a sequence which is a target for recombination) over a comparison window of at least 20 nucleotide positions, optionally over a window of at least 30–50 nucleotides, wherein the percentage of sequence identity is calculated by comparing the reference sequence to the polynucleotide sequence that may include deletions or additions which total 20 percent or less of the reference sequence over the window of comparison. The reference sequence may be a subset of a larger sequence.

Specific hybridization is defined herein as the formation, by hydrogen bonding or nucleotide (or nucleobase) bases, of hybrids between a probe polynucleotide (e.g., a polynucleotide of the invention and a specific target polynucleotide, wherein the probe preferentially hybridizes to the specific target such that, for example, a single band corresponding to, e.g., one or more of the RNA species of the gene (or specifically cleaved or processed RNA species) can be identified on a Northern blot of RNA prepared from a suitable source. Such hybrids may be completely or only partially base-paired. Polynucleotides of the invention which specifically hybridize to viral genome sequences may be prepared on the basis of the sequence data provided herein and available in the patent applications incorporated herein and scientific and patent publications noted above, and according to methods and thermodynamic principles known in the art and described in Sambrooke et al. et al., *Molecular Cloning: A Laboratory Manual*, 2nd Ed., (1989), Cold Spring Harbor, N.Y.; Berger and Kimmel, *Methods in Enzymology, Volume* 152. *Guide to Molecular Cloning Techniques* (1987), Academic Press, Inc., San Diego, Calif.; Goodspeed et al. (1989) Gene 76: 1; Dunn et al. (1989) *J. Biol. Chem.* 264: 13057, and Dunn et al. (988) *J. Biol. Chem.* 263: 10878, which are each incorporated herein by reference.

"Physiological conditions" as used herein refers to temperature, pH, ionic strength, viscosity, and like biochemical parameters that are compatible with a viable plant organism or agricultural microorganism (e.g., Rhizobium, Agrobacterium, etc.), and/or that typically exist intracellularly in a viable cultured plant cell, particularly conditions existing in the nucleus of said cell. In general, in vitro physiological conditions can comprise 50–200 mM NaCl or KCl, pH 6.5–8.5, 20–45° C. and 0.001–310 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s), metal chelators, nonionic detergents, membrane fractions, antifoam agents, and/or scintillants.

As used herein, the terms "label" or "labeled" refer to incorporation of a detectable marker, e.g., a radiolabeled amino acid or a recoverable label (e.g. biotinyl moieties that can be recovered by avid in or streptavidin). Recoverable labels can include covalently linked polynucleobase sequences that can be recovered by hybridization to a complementary sequence polynucleotide. Various methods of labeling polypeptides, PNAs, and polynucleotides are known in the art and may be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). In some embodiments, labels are attached by spacer arms of various lengths, e.g., to reduce potential steric hindrance.

As used herein, the term "statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer and/or may only be manifest in certain cell types.

The term "agent" is used herein to denote a chemical compound, a mixture of chemical compounds, a biological macromolecule, or an extract made from biological materials such as bacteria, plants, fungi, or animal cells or tissues. Agents are evaluated for potential activity as ADPGPP inhibitors or allosteric effectors by inclusion in screening assays described hereinbelow.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, the term "optimized" is used to mean substantially improved in a desired structure or function relative to an initial starting condition, not necessarily the optimal structure or function which could be obtained if all possible combinatorial variants could be made and evaluated, a condition which is typically impractical due to the number of possible combinations and permutations in polynucleotide sequences of significant length (e.g., a complete plant gene or genome).

As used herein, "ADPGPP enzymatic phenotype" means an observable or otherwise detectable phenotype that can be discriminative based on ADPGPP function. For example and not limitation, an ADPGPP enzymatic phenotype can comprise an enzyme Km for a substrate, Km for an inhibitor ($K_I$), Km for an activator (Ka), Vmax, a turnover rate, an inhibition coefficient (Ki), or an observable or otherwise detectable trait that reports ADPGPP function in a cell or clonal progeny thereof, including an adult plant or starch-storing organ thereof, which otherwise lack said trait in the absence of significant ADPGPP function.

As used herein, "complementing subunit" is used principally with reference to ADPGPP enzymes composed of S and L subunits and means an ADPGPP subunit of the opposite type (e.g., an S subunit can be a complementing subunit to an L subunit, and vice versa), wherein when the L and S subunits are present in a cell or in vitro reaction vessel under appropriate assay conditions they form a multimer having detectable ADPGPP activity. A complementing subunit can be obtained from the same taxonomic species of organism, or from a xenogenic species. Calibration assays are performed to determine whether a selected first subunit is a complementing subunit with respect to a second subunit; if the first subunit produces a detectable allosteric effect upon the activity, it is deemed for purposes of this disclosure to constitute a complementing subunit.

DETAILED DESCRIPTION OF THE INVENTION

The present invention provides methods, reagents, genetically modified plants, plant cells and protoplasts thereof, microbes, and polynucleotides, and compositions relating to the forced evolution of ADPGPP subunit sequences to improve an enzymatic property of a ADPGPP protein. In an aspect, the invention provides a shuffled ADPGPP L subunit which is catalytically active in the presence of a complementing S subunit, which may itself be shuffled, and which exhibits an improved enzymatic profile, such as an increased Km for inhibitor, decreased Km for activator, and or a decreased Km for substrate, increased Vmax, or the like.

In a broad aspect, the invention is based, in part, on a method for shuffling polynucleotide sequences that encode a ADPGPP subunit, such as an S subunit gene, L subunit gene, or combinations thereof. The method comprises the step of selecting at least one polynucleotide sequence that encodes an ADPGPP subunit having an enhanced enzymatic phenotype and subjecting said selected polynucleotide sequence to at least one subsequent round of mutagenesis and/or sequence shuffling, and selection for the enhanced phenotype. Preferably, the method is performed recursively on a collection of selected polynucleotide sequences encoding the ADPGPP subunit to iteratively provide polynucleotide sequences encoding ADPGPP subunit species having the desired enhanced enzymatic phenotype.

The invention provides shuffled ADPGPP encoding sequences, wherein said shuffled encoding sequences comprise at least 21 contiguous nucleotides, preferably at least 30 contiguous nucleotides, or more, of a first naturally occurring ADPGPP L gene sequence and at least 21 contiguous nucleotides, preferably at least 30 contiguous nucleotides, or more, of a second naturally occurring ADPGPP L gene sequence, operably linked in reading frame to encode an ADPGPP L subunit which has ADPGPP activity in the presence of a complementing S subunit and/or in the absence of said S subunit, and which has an enhanced enzymatic phenotype. In some variations, it will be possible to use shuffled encoding sequences which have less than 21 contiguous nucleotides identical to a naturally-occurring ADPGPP L gene sequence.

The invention also provides shuffled ADPGPP encoding sequences, wherein said shuffled encoding sequences comprise at least 21 contiguous nucleotides, preferably at least 30 contiguous nucleotides, or more, of a first naturally occurring ADPGPP S gene sequence and at least 21 contiguous nucleotides, preferably at least 30 contiguous nucleotides, or more, of a second naturally occurring ADPGPP S gene sequence, operably linked in reading frame to encode an ADPGPP S subunit which has a regulatory effect upon a complementing ADPGPP L subunit such that the multimer composed of the shuffled S subunit(s) and the L subunit(s) exhibit ADPGPP activity and wherein the multimer has an enhanced enzymatic phenotype. In some variations, it will be possible to use shuffled encoding sequences which have less than 21 contiguous nucleotides identical to a naturally-occurring ADPGPP gene sequence (s).

The invention provides shuffled ADPGPP S subunit encoding sequences, wherein the shuffled sequences comprise portions of a first parental ADPGPP encoding sequence which comprises at least one mutation in the encoding sequence as compared to the collection of predetermined naturally occurring ADPGPP S subunit sequences.

The invention provides shuffled ADPGPP L subunit encoding sequences, wherein the shuffled sequences comprise portions of a first parental ADPGPP S encoding sequence which comprises at least one mutation in the encoding sequence as compared to the collection of predetermined naturally occurring ADPGPP L subunit sequences.

Generally, the nomenclature used hereafter and the laboratory procedures in cell culture, molecular genetics, virology, and nucleic acid chemistry and hybridization described below are those well known and commonly employed in the art. Standard techniques are used for recombinant nucleic acid methods, polynucleotide synthesis, and microbial culture and transformation (e.g., biolistics, Agrobacterium (Ti plasmid), electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res*. 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference). Leaf PCR is suitable for genotype analysis of transgenote plants.

All sequences referred to herein or equivalents which function in the disclosed methods can be retrieved by GenBank database file designation or a commonly used reference name which is indexed in GenBank or otherwise published are incorporated herein by reference and are publicly available.

Incorporation by Reference of Related Applications

The following co-pending patent applications and publications of the present inventors and co-workers are incorporated herein by reference for all purposes: U.S. Ser. No. 08/198,431, filed 17 Feb. 1994, PCT/US95/0212 filed Feb. 17, 1995, WO97/20078, U.S. Pat. No. 5,605,793, U.S. Pat. No. 5,358,665, U.S. Pat. No. 5,270,170, U.S. Ser. No. 08/425,684 filed Apr. 18, 1995, U.S. Ser. No. 08/537,874 filed Oct. 30, 1995, U.S. Ser. No. 08/564,955 filed Nov. 30, 1995, U.S. Ser. No. 08/6621,859 filed Mar. 25, 1996, PCT/US96/05480 filed Apr. 18, 1996, U.S. Ser. No. 08/650,400 filed May 20, 1996, U.S. Ser. No. 08/675,502 filed Jul. 6, 1996, U.S. Ser. No. 08/721,824 filed Sep. 27, 1996, U.S. Ser. No. 08/722,660 filed Sep. 27, 1996, and U.S. Ser. No. 08/769,062 filed Dec. 18, 1996; WO 098/13485 and WO 098/13487; and Stemmer (1995) *Science* 270: 1510; Stemmer et al. (1995) *Gene* 164: 49–53; Stemmer (1995) *Bio/Technology* 13: 549–553: Stemmer(1994) *PNAS* 91: 10747–10751; Stemmer (1994) Nature 370: 389–391; Crameri et al. (1996) *Nature Medicine* 2: 1–3; Crameri et al. (1996) *Nature Biotechnology* 14: 315–319 and commonly assigned U.S. patent application U.S. Ser. No. 60/107,757 entitled "MODIFIED PHOSPHOENOLPYRUVATE CARBOXYLASE FOR IMPROVEMENT AND OPTIMIZA- TION OF PLANT PHENOTYPES," filed on Nov. 10, 1998; commonly assigned U.S. patent application U.S. Ser. No. 60/107,756 and 60/153,093 entitled "MODIFIED RIBULOSE BISPHOSPHATE CARBOXYLASE/OXYGENASE FOR IMPROVEMENT AND OPTIMIZATION OF PLANT PHENOTYPES," filed on Nov. 10, 1998 and Sep. 9, 1999, respectively; and "TRANSFORMATION, SELECTION, AND SCREENING OF SEQUENCE SHUFFLED POLYNUCLEOTIDES FOR DEVELOPMENT AND OPTIMIZATION OF PLANT PHENOTYPES" U.S. Ser. No. 60/098,528, PCT/US99/19732 and U.S. Ser. No. 09/385,833 filed Aug. 31, 1998, Aug. 30, 1999 and Aug. 30, 1999, respectively.

Overview

The invention relates in part to a method for generating novel or improved ADPGPP genetic sequences and improved starch production phenotypes which do not naturally occur or would be anticipated to occur at a substantial frequency in nature. A broad aspect of the method employs recursive nucleotide sequence recombination, termed "sequence shuffling", which enables the rapid generation of a collection of broadly diverse phenotypes that can be selectively bred for a broader range of novel phenotypes or more extreme phenotypes than would otherwise occur by natural evolution in the same time period. A basic variation of the method is a recursive process comprising: (1) sequence shuffling of a plurality of species of a genetic sequence, which species may differ by as little as a single nucleotide difference or may be substantially different yet retain sufficient regions of sequence similarity or site-specific recombination junction sites to support shuffling recombination, (2) selection of the resultant shuffled genetic sequence to isolate or enrich a plurality of shuffled genetic sequences having a desired phenotype(s), and (3) repeating steps (1) and (2) on the plurality of shuffled genetic sequences having the desired phenotype(s) until one or more variant genetic sequences encoding a sufficiently optimized desired phenotype is obtained. In this general manner, the method facilitates the "forced evolution" of a novel or improved genetic sequence to encode a desired ADPGPP enzymatic phenotype which natural selection and evolution has heretofore not generated in the reference agricultural organism.

Typically, a plurality of ADPGPP genetic sequences are shuffled and selected by the present method. The method can be used with a plurality of alleles, homologs, or cognate genes of a gentic locus, or even with a plurality or genetic sequences from related organisms, and in some instances with unrelated genetic sequences or portions thereof which have recombinogenic portions (either naturally or generated via genetic engineering). Furthermore, the method can be used to evolve a heterologous ADPGPP sequence (e.g., a non-naturally occurring mutant gene, or a subunit from another species) to optimize its function in concert with a complementing subunit, and/or in a particular host cell.

ADPGPP Embodiment—Lowered Km for substrate: Other features The invention provides an isolated polynucleotide encoding an enhanced ADPGPP protein having ADPGPP catalytic activity wherein the Km for a substrate (ATP, α-glucose- 1-phosphate (GIP)) is significantly lower than in a protein encoded by a parental polynucleotide encoding a naturally-occurring ADPGPP enzyme. Typically, the Km for substrate will be at least one-half logarithm unit lower than the parental sequence, preferably the Km will be at least one logarithm unit lower, and desirably the Km will be at least two logarithm units lower, or more. The isolated polynucleotide encoding an enhanced ADPGPP protein and in an expressible form can be transferred into a host plant, such as a crop species, wherein suitable expression of the polynucleotide in the host plant will result in improved starch biosynthesis efficiency as compared to the naturally-occurring host plant species, usually under certain conditions. The isolated polynucleotide can encode a single subunit ADPGPP, such as a bacterial form, or may encode a large (L) subunit or small (S) subunit of a multisubunit ADPGPP such as that found in green algae, and higher plants. The isolated polynucleotide can comprise a substantially full-length or full-length coding sequence substantially identical to a naturally occurring S gene and/or an L gene, typically comprising a shuffled L gene or a shuffled S gene, or both.

In a variation, the invention provides a polynucleotide comprising: (1) a sequence encoding a shuffled ADPGPP L subunit gene operably linked to a transcriptional regulatory sequence functional in a host cell, and further linked to (2) a selectable marker gene which affords a means of selection when expressed in host cells.

In a variation, the invention provides a polynucleotide comprising: (1) a sequence encoding a shuffled ADPGPP S subunit gene operably linked to a transcriptional regulatory sequence functional in a host cell, and further linked to (2) a selectable marker gene which affords a means of selection when expressed in host cells.

In a variation, the invention provides a polynucleotide comprising: (1) a sequence encoding a shuffled ADPGPP L subunit gene operably linked to a transcriptional regulatory sequence functional in a host cell, (2) a sequence encoding a shuffled ADPGPP S subunit gene operably linked to a transcriptional regulatory sequence functional in the host cell and, optionally, further linked to (3) a selectable marker gene which affords a means of selection when expressed in host cells.

In a variation, the invention provides an isolated polynucleotide encoding an enhanced ADPGPP protein having ADPGPP catalytic activity wherein the Km for a substrate is significantly lower than a protein encoded by a parental polynucleotide encoding a naturally-occurring ADPGPP enzyme or subunit. In an aspect, the enhanced ADPGPP protein is often an S subunit which is catalytically active in the presence of a complementing L subunit. In an aspect, the enhanced ADPGPP protein is a S subunit which is catalytically active in the absence of a complementing L subunit, such as for example, and not limitation, an ADPGPP S subunit which is at least 90 percent sequence identical to a naturally occurring ADPGPP subunit encoded by a genome of a plant or algae.

In a variation, the invention provides an isolated polynucleotide encoding an enhanced ADPGPP protein having ADPGPP catalytic activity wherein the Km (Ki)for an inhibitor (e.g., Pi) is significantly higher than a protein encoded by a parental polynucleotide encoding a naturally-occurring ADPGPP enzyme. In such embodiments, the concentration of inhibitor required to produce half-maximal inhibition of catalysis is typically at least one-half logarithm unit higher than a parental ADPGPP, often at least one log unit or more higher.

In a variation, the invention provides an isolated polynucleotide encoding an enhanced ADPGPP protein having ADPGPP catalytic activity wherein the Km for an activator (e.g., PGA, FBP) is significantly lower than in a protein encoded by a parental polynucleotide encoding a naturally-occurring ADPGPP enzyme. In such embodiments, the concentration of activator required to produce half-maximal activation of catalysis is typically at least one-half logarithm unit lower than a parental ADPGPP, often at least one log unit or more lower, in some embodiments at least two log units or more lower. In a variation, the shuffled ADPGPP protein possesses, in the substantial absence of activator, ADPGPP catalytic activity approximately equivalent to or greater than that of a naturally-occurring ADPGPP protein which is maximally stimulated with activator.

The invention provides an enhanced ADPGPP protein having ADPGPP catalytic activity wherein: (1) the Km for substrate is significantly lower than in a protein encoded by a parental polynucleotide encoding a naturally-occurring ADPGPP enzyme, and (2) the Km for inhibitor is significantly higher than a protein encoded by a parental polynucleotide encoding a naturally-occurring ADPGPP enzyme, and/or (3) the Km for activator is significantly lower than in a protein encoded by a parental polynucleotide encoding a naturally-occurring ADPGPP enzyme, and/or (4) the enhanced ADPGPP protein possesses a catalytic activity in the substantial absence of activator and inhibitor which is at least 25 percent or more greater than a naturally-occurring ADPGPP that is maximally stimulated with activator in the substantial absence of inhibitor; often the naturally-occurring ADPGPP used for comparison is an ADPGPP species which has an S subunit polypeptide that has the greatest percentage sequence identity to the shuffled S subunit polypeptide.

In an aspect, the invention provides a polynucleotide sequence encoding an shuffled S subunit of a plant or algal ADPGPP, wherein the shuffled S subunit, either alone and/or when reconstituted with a complementing L subunit, possesses a detectable enzymatic activity wherein: (1) the Km for substrate is significantly lower than in an S subunit protein encoded by a parental polynucleotide encoding a naturally-occurring ADPGPP enzyme, (2) the Km for an ADPGPP inhibitor is significantly higher than an S subunit protein encoded by a parental polynucleotide encoding a naturally-occurring ADPGPP enzyme, and/or (3) the Km for an ADPGPP activator is significantly lower than a S subunit protein encoded by a parental polynucleotide encoding a naturally-occurring ADPGPP enzyme S subunit, and/or (4) the Vmax for ADPGPP catalytic activity is substantially higher than the Vmax for ADPGPP catalytic activity of naturally-occurring ADPGPP under equivalent assay conditions (e.g., same concentration(s) of substrates, activators, and inhibitors) under at least one assay condition. In a variation, the shuffled S subunit requires a complementing L subunit for detectable enzymatic activity, or for increased enzymatic activity as compared to the activity of the shuffled S subunit in the absence of a complementing L subunit. In some embodiments, the shuffled S subunit sequences encode proteins that have an altered binding to, or allosteric interaction with, the complementing L subunit such that the binding constant for an inhibitor or activator on the L subunit may be substantially unchanged, however the shuffled S subunit, when reconstituted with L subunit, results in formation of an ADPGPP which has: (1) reduced sensitivity to inhibitors (e.g., Pi) and/or (2) enhanced sensitivity to activators (e.g., PGA) or (3) has ADPGPP activity which is insensitive to activator and possesses at least one ADPGPP catalytic activity (e.g., substrate $Km^{-1}$ or Vmax) which is at least 25 percent greater than that of a naturally-occurring ADPGPP that is maximally stimulated with activator in the substantial absence of inhibitor; often the naturally-occurring ADPGPP used for comparison is an ADPGPP species which has an S subunit polypeptide that has the greatest percentage sequence identity, among the collection of then known ADPGPP sequences, to the shuffled S subunit polypeptide.

In an aspect, the invention provides a polynucleotide sequence encoding an shuffled L subunit of ADPGPP, wherein the shuffled L subunit possesses the property of complexing with an unshuffled, complementing S subunit thereby resulting in a multimer (e.g., $L_2S_2$) having a detectable enzymatic activity wherein: (1) the Km for substrate is significantly lower than that of an ADPGPP protein containing an L subunit encoded by a parental polynucleotide encoding a naturally-occurring L subunit of ADPGPP, (2) the Vmax for ADPGGP catalytic activity is significantly higher than that of an ADPGPP protein containing an L subunit encoded by a parental polynucleotide encoding a naturally-occurring L subunit of ADPGPP under similar assay conditions, and/or (3) the Km for activator is significantly lower than that of an ADPGPP protein containing an L subunit encoded by a parental polynucleotide encoding a naturally-occurring L subunit of ADPGPP, and/or (4) the Km for inhibitor is significantly higher than that of an ADPGPP protein containing an L subunit encoded by a parental polynucleotide encoding a naturally-occurring L subunit of ADPGPP, and/or (5) the Vmax for ADPGPP catalytic activity is substantially higher than the Vmax for ADPGPP catalytic activity of naturally-occurring ADPGPP under equivalent assay conditions (e.g., same concentration (s) of substrates, activators, and inhibitors) under at least one assay condition. In some embodiments, the shuffled L subunit sequences encode proteins that have an altered binding to, or allosteric interaction with, the complementing S subunit such that the binding constant for an inhibitor or activator on the L subunit may be substantially unchanged, however the shuffled L subunit, when reconstituted with S subunit, results in formation of an ADPGPP which has: (1) reduced sensitivity to inhibitors (e.g., Pi) and/or (2) enhanced sensitivity to activators (e.g., PGA) or (3) has ADPGPP activity which is insensitive to activator and possesses at least one ADPGPP catalytic activity (e.g., substrate $Km^-$ or Vmax) which is at least 25 percent greater than that of a naturally-occurring ADPGPP that is maximally stimulated with activator in the substantial absence of inhibitor; often the naturally-occurring ADPGPP used for comparison is an ADPGPP species which has an L subunit polypeptide that has the greatest percentage sequence identity, among the collection of then known ADPGPP sequences, to the shuffled L subunit polypeptide. In some embodiments, the binding constant for an inhibitor, activator, and/or substrate will be at least one-half log unit higher or lower than an equivalent naturally occurring ADPGPP of greatest sequence homology (percent sequence identity) to the shufflant subunit(s).

In an aspect, the invention provides an improved S subunit of an ADPGPP, or shufflant thereof, and a polynucleotide encoding same. In some embodiments, the polynucleotide will be operably linked to a transcription regulation sequence forming an expression construct, which may be linked to a selectable marker gene; for embodiments where it is useful to target a bacterial ADPGPP shufflant into plant cell plastids or tuber or other specialized organs where starch synthesis is prominent, a sequence encoding a chloroplast transit peptide (CTP), such as that derived from Arabidopsis rbcS gene, is fused in-frame to the shufflant ADPGPP sequence, to ensure delivery of the S subunit to the appropriate compartment/organ. In some embodiments, such a polynucleotide is present as an integrated transgene in a plant chromosome in a format for expression and processing of the S subunit. It can be desirable for such a polynucleotide transgene to be transmissible via germline transmission in a plant; in the case of ADPGPP S gene sequences transferred to a plant or algal cells, it is often accompanied by a selectable marker gene which affords a means to select for progeny which retain the transferred shuffled ADPGPP S gene sequence. In some embodiments, the transferred shuffled ADPGPP S gene sequence is derived by shuffling a pool of parental sequences, at least one of which encodes a bacterial ADPGPP subunit. Often, the transcription control sequences comprise tuber-specific or seed-specific promoters to overcome possible detrimental effects of constitutive expression.

In an aspect, the invention provides an improved S subunit of an ADPGPP, or shufflant thereof, wherein the improved S subunit has at least 80% sequence identity to the polypeptide sequence of a naturally-occurring plant ADPGPP S subunit, and which has an enhanced ADPGPP enzymatic phenotype; and a polynucleotide encoding same. In some embodiments, the polynucleotide will be operably linked to a transcription regulation sequence forming an expression construct, which may be linked to a selectable marker gene. In some embodiments, such a polynucleotide is present as an integrated transgene in a plant chromosome. It can be desirable for such a polynucleotide transgene to be transmissible via germline transmission in a plant. Often, the transcription control sequences comprise tuber-specific or seed-specific promoters to overcome possible detrimental effects of constitutive expression.

In an aspect, the invention provides an improved L subunit of a plant ADPGPP, or shufflant thereof, and a polynucleotide encoding same. In some embodiments, the polynucleotide will be operably linked to a transcription regulation sequence forming an expression construct, which may be linked to a selectable marker gene. In some embodiments, such a polynucleotide is present as an integrated transgene in a plant chromosome. It can be desirable for such a polynucleotide transgene to be transmissible via germline transmission in a plant.

In an aspect, the invention provides a hybrid S subunit composed of a shufflant comprising a sequence of at least 25 contiguous nucleotides at least 95 percent identical to a plant ADPGPP S gene and a sequence of at least 25 contiguous nucleotides at least 95 percent identical to a bacterial or algal ADPGPP gene, and a polynucleotide encoding same, and typically encoding a substantially full-length ADPGPP S subunit protein, usually comprising at least 90 percent of the coding sequence length, but not necessarily sequence identity, of a naturally occurring ADPGPP S protein. In some embodiments, the polynucleotide will be operably linked to a transcription regulation sequence forming an expression construct, which may be linked to a selectable marker gene. In some embodiments, such a polynucleotide is present as an integrated transgene in a plant chromosome. It can be desirable for such a polynucleotide transgene to be transmissible via germline transmission in a plant.

The invention provides expression constructs, including bacterial plasmids, shuttle vectors, and plant transgenes, wherein the expression construct comprises a transcriptional regulatory sequence functional in plants operably linked to a polynucleotide encoding an enhanced ADPGPP protein subunit. With respect to polynucleotide sequences encoding ADPGPP S subunit proteins, it is generally desirable to express such encoding sequences in plant cells with the expression constructs containing the necessary sequences for appropriate transcription, translation, and processing, which can include translocation to a plastid or other organ compartment. The invention further provides plants and plant germplasm comprising said expression constructs, typically in stably integrated or other replicable form which segregates and can be stably maintained in the host organism, although in some embodiments it is desirable for commercial reasons that the expression sequence not be in the germline of sexually reproducible plants.

The invention provides a method for obtaining an isolated polynucleotide encoding an enhanced ADPGPP protein having ADPGPP catalytic activity wherein the Km for substrate is significantly lower than a protein encoded by a parental polynucleotide encoding a naturally-occurring ADPGPP enzyme, the method comprising: (1) recombining sequences of a plurality of parental polynucleotide species encoding at least one ADPGPP sequence under conditions suitable for sequence shuffling to form a resultant library of sequence-shuffled ADPGPP polynucleotides, (2) transferring said library into a plurality of host cells forming a library of transformants wherein sequence-shuffled ADPGPP polynucleotides are expressed, (3) assaying individual or pooled transformants for ADPGPP catalytic activity to determine the relative or absolute Km for substrate and identifying at least one enhanced transformant that expresses a ADPGPP activity which has a significantly lower Km for substrate than the ADPGPP activity encoded by the parental sequence (s), (4) recovering the sequence-shuffled ADPGPP polynucleotide from at least one enhanced transformant. Optionally, the recovered sequence-shuffled ADPGPP polynucleotide encoding an enhanced ADPGPP is recursively shuffled and selected by repeating steps 1 through 4, wherein the recovered sequence-shuffled ADPGPP polynucleotide is used as at least one parental sequence for subsequent shuffling. If it is desired to obtain a sequence-shuffled ADPGPP encoding a ADPGPP enzyme having an increased Km for inhibitor, step 3 comprises assaying individual or pooled transformants for ADPGPP catalytic activity to determine the relative or absolute Km for the inhibitor and identifying at least one enhanced transformant that expresses a ADPGPP activity which has a significantly higher Km for inhibitor than the ADPGPP activity encoded by the parental sequence (s). Similarly, if it is desired to obtain a sequence-shuffled ADPGPP encoding a ADPGPP enzyme having a decreased Km for activator, step 3 comprises assaying individual or pooled transformants for ADPGPP catalytic activity to determine the relative or absolute Km for activator, and identifying at least one enhanced transformant that expresses an ADPGPP activity which has a significantly lower Km for activator than the ADPGPP activity encoded by the parental sequence(s).

In an aspect, the method is used to generate sequence-shuffled ADPGPP polynucleotides encoding a single subunit ADPGPP which is catalytically active in the absence of heterologous proteins. For example and not limitation, a bacterial or algal single subunit ADPGPP gene, such as that from *E coli* encoded by the glgC gene, is shuffled and selected for the desired ADPGPP phenotype (e.g., altered catalytic or regulatory property, or function in a predetermined plant host). The parental single subunit ADPGPP encoding sequence(s) may be shuffled alone or in combination with one or more higher plant ADPGPP subunit sequences (L or S), preferably those non-bacterial sequences having regions of at least 70 percent sequence identity. In an embodiment, a parental ADPGPP encoding sequence employed for generating shufflants comprises an ADPGPP allosteric mutant from *E. coli* (e.g., SG14, Ala44Thr; CL1136, Arg67Cys; SG5, Pro295 Ser; or 618, Gly336 Asp), *Salmonella typhimurium* (Steiner et al. (1977) *J. Bact.* 129:

246), or the green algae *Clhlamodomonas reinhardtii* (Ball et al. (1991) *Planta* 185: 17). Additionally, ADPGPP gene sequences from *Rhodobacter spheroides* or *Rhodospirillum rubrum* can be used. The ADPGPP shufflants are transferred into a suitable host cell for expression and selection of the desired ADPGPP phenotype; in an embodiment, the host cells are *E coli* strains lacking endogenous ADPGPP activity (e.g., LCB618, strains carrying glgC3 mutation or glgC mutation, and the like). In an embodiment, the host cells constitutively or inducibly express a complementing ADPGPP subunit (e.g., S or L) to functionally complement the shufflant sequences encoding a subunit of a multisubunit form of ADPGPP.

In an aspect, the ADPGPP gene sequence(s) is/are obtained as an isolated polynucleotide and is shuffled by any suitable shuffling method known in the art, such as DNA fragmentation and PCR, error-prone PCR, and the like, preferably with one or more additional parental polynucleotides encoding all or a part of another ADPGPP species, which may be a single subunit ADPGPP, or one subunit of a multisubunit ADPGPP, such as a plant L or S subunit. The population of sequence-shuffled ADPGPP polynucleotides are each operably linked to an expression sequence and transferred into host cells, preferably host cells substantially lacking endogenous ADPGPP activity, such as a deletion strain of *E coli*, wherein the sequence-shuffled ADPGPP polynucleotides are expressed, forming a library of sequence-shuffled ADPGPP transformants. A sample of individual transformants and/or their clonal progeny are isolated into discrete reaction vessels for ADPGPP activity assay, or are assayed in situ in certain embodiments. For samples assayed in reaction vessels, aliquots of the samples are separated into a plurality of reaction vessels containing an approximately equimolar amount of ADPGPP or total protein, and each vessel is assayed for ADPGPP activity in the presence of a predetermined concentration of substrate which ranges from about 0.0001 times the predetermined Km for substrate of the ADPGPP encoded by the parental polynucleotide(s) to about 10,000 times the predetermined Km for substrate of the ADPGPP encoded by the parental polynucleotide(s); the plurality of reaction vessels for each shufflant sample may also contain a fixed or variable concentration of activator and/or inhibitor, or neither. From the data generated by assaying the plurality of reaction vessels containing aliquots of each transformant, a Km value and/or Vmax is calculated by conventional art-known means for the sequence-shuffled ADPGPP of each transformant; typically the Km and Vmax values for a specific inhibitor or activator are determined. Sequence-shuffled polynucleotides encoding ADPGPP proteins that have significantly decreased Km and/or Vmax values for substrate, and/or significantly increased Km values of inhibitor, and/or significantly decreased Km values for activator are selected and used as parental sequences for at least one additional round of sequence shuffling by any suitable method and selection for further optimization of the desired ADPGPP phenotype. The shuffling and selection process is performed iteratively until sequence shuffled polynucleotides encoding at least one ADPGPP enzyme having a desired ADPGPP enzymatic phenotype is obtained, or until the optimization to reduce the relevant Km (or increase Vmax) has plateaued and no further improvement is seen in subsequent rounds of shuffling and selection.

In a variation, the sequence-shuffled polynucleotides operably linked to an expression sequence is also linked, in polynucleotide linkage, to an expression cassette encoding a selectable marker gene. Transformants are propagated on a selective medium to ensure that transformants which are assayed for ADPGPP activity contain a sequence-shuffled ADPGPP encoding sequence in expressible form. In embodiments wherein a polynucleotide encoding a bacterial ADPGPP are to be introduced into host cells which possess plastids, the ADPGPP encoding sequence is generally operably linked to a transport sequence to facilitate transport of the translated gene product into the plastid. Optionally, a transcriptional regulatory sequence functional in chloroplasts may be used and the resultant expression cassette is transferred into the host cell plastids, such as by biolistics, polyethylene glycol (PEG) treatment of protoplasts, or an other suitable method.

In a variation, the above-described method is modified such that ADPGPP activity is assayed in the presence of varying concentrations of inhibitor and the Km for inhibitor is determined. Each vessel containing an aliquot of a transformant is assayed for ADPGPP activity in the presence of a predetermined concentration of inhibitor which ranges from about 0.0001 times the predetermined Km for inhibitor of the ADPGPP encoded by the parental polynucleotide(s) to about 10,000 times the predetermined Km for inhibitor of the ADPGPP encoded by the parental polynucleotide(s). From the data generated by assaying the plurality of reaction vessels containing aliquots of each transformant, a Km value is calculated by conventional art-known means for the sequence-shuffled ADPGPP of each transformant. Sequence-shuffled polynucleotides encoding ADPGPP proteins that have significantly increased Km values for inhibitor are selected and used as parental sequences for at least one additional round of sequence shuffling by any suitable method and selection for increased Km values for inhibitor. The shuffling and selection process is performed iteratively until sequence shuffled polynucleotides encoding at least one ADPGPP enzyme having a desired Km value is obtained, or until the optimization to increase the Km has plateaued and no further improvement is seen in subsequent rounds of shuffling and selection.

In a variation, the above-described method is modified such that ADPGPP activity is assayed in the presence of varying concentrations of activator and the Km for activator is determined. Each vessel containing an aliquot of a transformant is assayed for ADPGPP activity in the presence of a predetermined concentration of activator which ranges from about 0.0001 times the predetermined Km for activator of the ADPGPP encoded by the parental polynucleotide(s) to about 10,000 times the predetermined Km for activator of the ADPGPP encoded by the parental polynucleotide(s). From the data generated by assaying the plurality of reaction vessels containing aliquots of each transformant, a Km value is calculated by conventional art-known means for the sequence-shuffled ADPGPP of each transformant. Sequence-shuffled polynucleotides encoding ADPGPP proteins that have significantly decreased Km values for activator are selected and used as parental sequences for at least one additional round of sequence shuffling by any suitable method and selection for decreased Km values for activator. The shuffling and selection process is performed iteratively until sequence shuffled polynucleotides encoding at least one ADPGPP enzyme having a desired Km value is obtained, or until the optimization to increase the Km has plateaued and no further improvement is seen in subsequent rounds of shuffling and selection.

In a variation, the method comprises conducting biochemical assays on sample aliquots of transformants to determine ADPGPP enzyme activity so as to establish the ratio of the Km for activator to the Km for inhibitor for individual transformants. Sequence-shuffled polynucleotides encoding ADPGPP are obtained from transformants exhibiting a decrease in said ratio as compared to the ratio in ADPGPP produced from the parental encoding polynucleotide(s) to provide selected sequence-shuffled ADPGPP polynucleotides which can be used as parental sequences for at least one additional round of sequence shuffling by any suitable method and selection for a decreased ratio of Km(activator) to Km(inhibitor). The shuffling and selection process is performed iteratively until sequence shuffled polynucleotides encoding at least one ADPGPP enzyme having a desired Km ratio is obtained, or until the optimization to decrease the Km ratio has plateaued and no further improvement is seen in subsequent rounds of shuffling and selection.

In an embodiment of the method, the host cell for transformation with sequence-shuffled polynucleotides encoding ADPGPP is a bacterial mutant which lacks a functional ADPGPP subunit protein, such as $E\ coli$ glygogen$^{(-)}$mutant or an equivalent. For such mutant host cells, transformants which express ADPGPP activity and permit glycogen synthesis can be readily identified as blue colonies following exposure to iodine vapor, with the degree of blue color serving as a proxy of the degree of ADPGPP activity. In this variation, blue colonies identified after exposure to iodine vapor, or their replicate colonies, are selected and assayed in vitro to determine whether, relative to a parental ADPGPP assayed under equivalent conditions, the Km of inhibitor is increased and/or the Km for activator is decreased for each shufflant transformant; transformants which exhibit an increased Km(inhibitor) and/or a decreased Km(activator) are selected and used for at least one subsequent round of sequence shuffling and ADPGPP enzymatic phenotype selection. Often inhibitor-relief shufflants (Km for inhibitor is significantly higher than parental) are pooled with each other and reshuffled, as are, separately, activator-relief shufflants (Km for activator is significantly decreased compared to parental); sometimes inhibitor-relief shufflants and activator-relief shufflants are pooled with each other.

In an embodiment of the method, the host cell comprises a cell expressing a complementing subunit of ADPGPP which is capable of interacting with an ADPGPP protein encoded by sequence-shuffled polypeptides encoding an ADPGPP subunit. For example, if the shuffled polynucleotides encode a large subunit of ADPGPP, a host cell for the transformation may endogenously encode a small subunit of ADPGPP that may interact with a functional large subunit encoded by the shuffled polynucleotides. It is often desirable that such host cells lack expression of the endogenous ADPGPP subunit corresponding to (e.g., cognate to) the type of subunit encoded by the shuffled polynucleotides. Mutant cell lines are available in the art and novel mutant ADPGPP-deficient cells can be obtained by selecting from a pool of mutagenized cells those mutants which have lost detectable ADPGPP activity, or by homologous gene targeting of ADPGPP L and/or S genes.

In an embodiment of the method, polynucleotides encoding naturally-occurring ADPGPP protein sequences of a plurality of species of photosynthetic prokaryotes and/or algae and/or higher plants are shuffled by a suitable shuffling method to generate a shuffled ADPGPP polynucleotide library, wherein each shuffled ADPGPP encoding sequence is operably linked to an expression sequence, and which may optionally comprise a linked selectable marker gene cassette. Said library is transformed into a host cell population, such as bacteria which lack endogenous ADPGPP activity, to form a transformed host cell library. The transformed host cell library is propagated on growth medium, which may contain a selection agent to ensure retention of a linked selectable marker gene. The transformed host cell library is subjected to selection by incubating the cells under a graded range of concentrations of iodine vapor and selecting blue colonies, preferentially those having the deepest coloration of blue. Transformed host cells which are screened for under the most stringent conditions are isolated individually or in pools, and the sequence-shuffled polynucleotide sequences encoding ADPGPP are recovered, and optionally subjected to at least one subsequent iteration of shuffling and selection on growth medium, optionally using lower ranges of iodine vapor pressure (or exposure times) to identify blue colonies. Optionally, or in addition, transformants are assayed for inhibitor-resistant ADPGPP activity and/or high activity ADPGPP in absence of activator. The recovered sequence-shuffled ADPGPP polynucleotide(s) encode(s) an enhanced ADPGPP subunit protein.

In an embodiment of the method, a host cell comprising a non-photosynthetic bacterium, such as $E\ coli$, lacking an endogenous ADPGPP activity, is transformed with an expression cassette encoding the production of a complementing ADPGPP subunit (e.g., S if host cells are to be used with a library of shuffled L genes, and vice-versa), thereby forming a complementing host cell. Usually, a linked selectable marker and selection conditions are employed to retain the expression cassette in the complementing host cells and their progeny. ADPGPP encoding sequences are selected by the skilled artisan from publicly available sources. The method further comprises transforming a population of complementing host cells with a library of shuffled ADPGPP-encoding polynucleotides, each ADPGPP shufflant polynucleotide encoding a species of a shuffled ADPGPP subunit (S, if the complementing subunit expressed in the host cells is L; L, if the complementing subunit expressed in the host cells is S), then operably linked to a transcriptional control sequence forming a subunit expression cassette, culturing the population of transformed complementing host cells for a suitable incubation period, determining the amount of ADPGPP activity in each transformed host cell and its clonal progeny relative to the amount of ADPGPP in untransformed complementing host cells cultured under equivalent conditions, including culture medium, atmosphere, incubation time and temperature, and selecting from said population of transformed complementing host cells and their clonal progeny cells which exhibit ADPGPP at statistically significant increased amount relative to said untransformed complementing host cells, and segregating or isolating said selected transformed complementing host cells thereby forming a selected subpopulation of host cells harboring selected shuffled polynucleotides encoding ADPGPP subunit protein species having enhanced catalytic ability; said selected shuffled polynucleotides can be recovered and optionally subjected to additional rounds of shuffling and selection for enhanced ADPGPP catalytic or regulatory function to provide one or more optimized shuffled subunit encoding sequences. In a variation, the transformed complementing host cells are segregated in culture vessels, such as a multimicrowell plate, wherein each vessel comprises a subpopulation of species of transformed complementing host cells and their clonal progeny, often consisting of a single species of transformed complementing host cell and its clonal progeny, if any. Typically, the expression cassettes encoding the shuffled ADPGPP subunit proteins are linked to a selectable marker gene cassette and selection is applies, typically by selection with an antibiotic in the culture medium, to reduce the prevalence of untransformed cells.

The invention provides a plant cell protoplast and clonal progeny thereof containing a sequence-shuffled polynucleotide encoding a ADPGPP subunit which is not encoded by the naturally occurring genome of the plant cell protoplast. The invention also provides a collection of plant cell protoplasts transformed with a library of sequence-shuffled ADPGPP subunit polynucleotides in expressible form. The invention further provides a plant cell protoplast co-transformed with at least two species of library members wherein a first species of library members comprise sequence-shuffled ADPGPP large subunit polynucleotides and a second species of library members comprise sequence-shuffled ADPGPP small subunit polynucleotides. In an embodiment, the subunit polynucleotides are transferred into a plastid compartment for expression and processing, such as by transfer into chloroplasts in a format suitable for expression in the plastid, such as for example and not limitation as a recombinogenic construct for general targeted recombination into a chloroplast chromosome. Alternatively, the subunit proteins encoded by the expression cassettes comprise a chloroplast transit peptide sequence to facilitate transfer of the encoded proteins into the plastid (or other) compartment.

The invention also provides a regenerated plant containing at least one species of replicable or integrated polynucleotide comprising a sequence-shuffled portion and encoding a ADPGPP subunit polypeptide. The invention provides a method variation wherein at least one round of phenotype selection is performed on regenerated plants derived from protoplasts transformed with sequence-shuffled ADPGPP subunit library members. In an embodiment, the phenotype selection comprises a determination, either directly or by proxy, of starch content in a storage tissue (e.g., tuber or seed), or microscopic detection of starch granule size and/or abundance.

The invention provides species-specific ADPGPP shuffling, wherein a transformed plant cell or adult plant or reproductive structure comprises a polynucleotide encoding a shuffled ADPGPP subunit that is at least 95 percent sequence identical to the corresponding ADPGPP subunit encoded by an untransformed naturally-occurring genome of the same taxonomic species of plant cell or adult plant. Typically, the shuffled ADPGPP subunit results from shuffling of one or more alleles encoding the ADPGPP subunit in the taxonomic species genome, optionally including mutagenesis in one or more of the iterative shuffling and selection cycles. The species-specific ADPGPP shuffling may include shuffling a polynucleotide encoding a full-length ADPGPP subunit of a first taxonomic species under conditions whereby ADPGPP subunit sequences of a second taxonomic species (or collection of species) are shuffled in at a low prevalence, such that the resultant population of shufflant polynucleotides contains, on average, shuffled polynucleotides composed of at least about 95 percent sequence encoding the first taxonomic species ADPGPP subunit and less than about 5 percent sequence encoding the second taxonomic species (or collection of species) ADPGPP subunit. The species-specific shufflants are thus highly biased towards identity with the first taxonomic species and shufflants which are selected for the desired ADPGPP phenotype are transferred back into the first taxonoic species for expression and regeneration of adult plants and germplasm. Optionally, selected shufflants are back-crossed against the naturally occurring ADPGPP encoding sequences of the first taxonomic species to remove non-essential sequence alterations and harmonize the final shufflant sequence to the naturally-occurring ADPGPP sequence of the first taxonomic species.

A variation of the method includes adapting a bacterial or algal ADPGPP for optimal function in a plant cell, or adult vegetative plant. This variation comprises recursive shuffling and selection of a library of bacterial or algal ADPGPP encoding sequences in a plant cell of the taxonomic species of plant for which the bacterial or algal ADPGPP is being adapted to function in an adult plant. This variation can include not only selecting for a desired ADPGPP enzymatic phenotype, but also selecting for appropriate function of a operably linked transcriptional control sequence, such as a tuber-specific (e.g., patatin promoter) or a seed-specific transcriptional control element in conjunction with ADPGPP function. This variation can employ host cells which are regenerable post-transformation and selection of adult plants for high starch content storage tissues; recovery of the encoding ADPGPP shufflants (and optionally the linked transcriptional control sequences), and at least one cycle of recursive shuffling and selection to evolve a bacterial or algal ADPGPP, and optionally a transcriptional control sequence, optimized for function in the desired plant taxonomic species or closely related taxonomic categories.

An object of the invention is the production of higher plants which express one or more ADPGPP enzyme subunits which confer an enhanced starch conversion ratio (or net starch storage amount) to the plants. Although the invention is described principally with respect to the use of genetic sequence shuffling to generate enhanced ADPGPP coding sequences, the invention also provides for the introduction of ADPGPP coding sequences obtained from organisms having ADPGPP with desirable enzymatic phenotypes, such as inhibitor-resistant ADPGPP from bacterial mutants, into higher plants. Thus, the invention provides a method comprising the step of introducing into a higher plant (e.g., a monocot or dicot) an expression cassette encoding an ADPGPP encoded by a genome of a bacterium or algae. Typically, at least a sequence encoding a substantially full-length large subunit of the bacterial or algal ADPGPP is transferred. An aspect of the invention provides C4 land plants comprising a polynucleotide sequence encoding a bacterial or algal ADPGPP composed in an expression cassette suitable for expression in chloroplasts of the C4 land plant; optionally an expression cassette encoding an ADPGPP subunit operably linked to regulatory sequences for expression in the nucleus of the C4 plant additionally is transferred into the nucleus of the C4 plant. The ADPGPP expression cassette is transferred into the chloroplasts or nucleus of a regenerable plant cell (e.g. a protoplast of a C4 plant cell) by art-known transformation methods. A C3 plant may be used in place of a C4 plant if desired. A specific embodiment comprises a regenerable protoplast of *Glycine max, Nicotiana tabacum*, or *Zea mays* (or other agricultural crop species amenable to regeneration from protoplasts) having a chloroplast or nuclear genome containing an expressible shuffled ADPGPP subunit gene that is obtained from a bacterium or algae, and typically is at least 90 percent up to 99 percent sequence identical to an ADPGPP subunit gene in the genome of said bacterium or algae, but is mutated in at least one codon as compared to the parental sequence. The invention also provides adult plants, cultivars, seeds, vegetative bodies, fruits, germplasm, and reproductive cells obtained from regeneration of such transformed protoplasts.

The invention provides a kit for obtaining a polynucleotide encoding a ADPGPP protein, or subunit thereof, having a predetermined enzymatic phenotype, the kit comprising a cell line suitable for forming transformable host cells and a collection sequence-shuffled polynucleotides formed by in vitro sequence shuffling. The kit often further comprises a transformation enhancing agent (e.g., lipofection agent, PEG, etc.) and/or a transformation device (e.g., a biolistics gene gun) and/or a plant viral vector which can infect plant cells or protoplasts thereof.

The disclosed method for providing an agricultural organism having an improved ADPGPP enzymatic phenotype by iterative gene shuffling and phenotype selection is a pioneering method which enables a broad range of novel and advantageous agricultural compositions, methods, kits, uses, plant cultivars, and apparatus which will be apparent to those skilled in the art in view of the present disclosure.

ADPGPP

Coding sequences for L and S subunits for various species are disclosed in the literature and Gerbank, among other public sources, and may be obtained by cloning, PCR, or from available deposited materials.

ADPGPP subunit shufflants are generated by any suitable shuffling method from one or more parental sequences, optionally including mutagenesis, and the resultant shufflants are introduced into a suitable host cell, typically in the form of expression cassettes wherein the shuffled polynucleotide sequence encoding the ADPGPP subunit is operably linked to a transcriptional regulatory sequence and any necessary sequences for ensuring transcription, translation, and processing of the encoded ADPGPP subunit protein. Each such expression cassette or its shuffled ADPGPP encoding sequence can be referred to as a "library member" composing a library of shuffled ADPGPP subunit sequences. The library is introduced into a population of host cells, such that individual host cells receive substantially one or a few species of library member(s), to form a population of shufflant host cells expressing a library of shuffled ADPGPP subunit species. The population of shufflant host cells is screened so as to isolate or segregate host cells and/or their progeny which express ADPGPP subunit(s) having the desired enhanced phenotype. The shuffled ADPGPP subunit encoding sequence(s) is/are recovered from the isolated or segregated shufflant host cells, and typically subjected to at least one subsequent round of mutagenesis and/or sequence shuffling, introduced into suitable host cells, and selected for the desired enhanced enzymatic phenotype; this cycle is generally performed iteratively until the shufflant host cells express an ADPGPP subunit having the desired level or enzymatic phenotype or until the rate of improvement in the desired enzymatic phenotype produced by shuffling has substantially plateaued. The shufflant ADPGPP polynucleotides expressed in the host cells following the iterative process of shuffling and selection encode ADPGPP subunit specie(s) having the desired enhanced phenotype.

For illustration and not to limit the invention, examples of a desired ADPGPP enzymatic phenotype can include increased substrate usage rate at a given substrate concentration, decreased inhibition by an ADPGPP inhibitor (desensitization), increased Km for inhibitor (desensitization), increased activation by an activator (desensitization), decreased Km for activator (desensitization), complete lack of need for activation (desensitization), decreased ratio of Km for activator to Km for inhibitor, velocity (Vmax) for substrate use, and the like as described herein and as may be desired by the skilled artisan.

Shuffling

The following publications describe a variety of recursive recombination procedures and/or methods which can be incorporated into such procedures, e.g., for shuffling of ADPGPP genes and gene fragments as herein: Stemmer, et al., (1999) "Molecular breeding of viruses for targeting and other clinical properties. Tumor Targeting" 4:1–4; Nesset al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameriet al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proceedings of the National Academy of Sciences, U.S.A.* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: *The Encyclopedia of Molecular Biology*. VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxyribonucleotides" *Gene*, 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proceedings of the National Academy of Sciences. U.S.A.* 91:10747–10751.

Additional details regarding DNA shuffling methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "COMPOSITIONS FOR CELLULAR AND METABOLIC ENGINEERING."

In addition, details and formats for DNA shuffling are found in a variety of PCT and foreign patent application publications, including: Stemmer and Crameri, "DNA MUTAGENESIS BY RANDOM FRAGMENTATION AND REASSEMBLY" WO 95/22625; Stemmer and Lipschutz "END COMPLEMENTARY POLYMERASE CHAIN REACTION" WO 96/33207; Stemmer and Crameri "METHODS FOR GENERATING POLYNUCLEOTIDES HAVING DESIRED CHARACTERISTICS BY ITERATIVE SELECTION AND RECOMBINATION" WO 97/20078; Minshull and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION" WO 99/41383; Punnonen et al. "GENETIC VACCINE VECTOR ENGINEERING" WO 99/41369; Punnonen et al. OPTIMIZATION OF IMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGANISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO 9813487.

Certain U.S. Applications provide additional details regarding DNA shuffling and related techniques, including "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407,800; "EVOLUTION OF WHOLE CELLS AND ORGANISMS BY RECURSIVE SEQUENCE RECOMBINATION", by del Cardyre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392; and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393, and "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118854) and "METHODS FOR MAKING CHARACTER STRINGS, POLYNUCLEOTIDES & POLYPEPTIDES HAVING DESIRED CHARACTERISTICS" by Selifonov et al. filed Oct. 12, 1999 (U.S. Ser. No. 09/416375).

As review of the foregoing publications, patents, published applications and U.S. patent applications reveals, recursive recombination and selection of nucleic acids to provide new nucleic acids with desired properties can be carried out by a number of established methods. Any of these methods can be adapted to the present invention to evolve ADPGPP coding nucleic acids or homologues to produce new enzymes with improved properties. Both the methods of making such enzymes and the enzymes or enzyme coding libraries produced by these methods are a feature of the invention.

In brief, at least 5 different general classes of recombination methods are applicable to the present invention. First, nucleic acids can be recombined in vitro by any of a variety of techniques discussed in the references above, including e.g., DNAse digestion of nucleic acids to be recombined followed by ligation and/or PCR reassembly of the nucleic acids. Second, nucleic acids can be recursively recombined in vivo, e.g., by allowing recombination to occur between nucleic acids in cells. Third, whole cell genome recombination methods can be used in which whole genomes of cells are recombined, optionally including spiking of the genomic or chloroplast recombination mixtures with desired library components such as ADPGPP encoding nucleic acids. Fourth, synthetic recombination methods can be used, in which oligonucleotides corresponding to different ADPGPP homologues are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Fifth, in silico methods of recombination can be affected in which genetic algorithms are used in a computer to recombine sequence strings which correspond to ADPGPP homologues. The resulting recombined sequence strings are optionally converted into nucleic acids by synthesis of nucleic acids which correspond to the recombined sequences, e.g., in concert with oligonucleotide synthesis/gene reassembly techniques. Any of the preceding general recombination formats can be practiced in a reiterative fashion to generate a more diverse set of recombinant nucleic acids.

A basic format of the method, termed sequence shuffling (or simply "shuffling"), in broad application, consists of a method for generating a selected polynucleotide sequence or population of selected polynucleotide sequences, typically in the form of amplified and/or cloned polynucleotides, whereby the selected polynucleotide sequence(s) possess or encode a desired phenotypic characteristic (e.g., encode a polypeptide, promote transcription of linked polynucleotides, modify transformation efficiency, bind a protein, and the like) which can be selected for. One method of identifying polypeptides that possess a desired structure or functional property, such as encoding a desired enzymatic function(s) (e.g., an enhanced ADPGPP, a herbicide catabolizing enzyme, an optimized plant biosynthetic pathway), involves the screening of a large library of polynucleotides for individual library members which possess or encode the desired structure or functional property conferred by the polynucleotide sequence.

In a general aspect, the invention provides a method, termed "sequence shuffling", for generating libraries of recombinant polynucleotides having a desired ADPGPP enzyme characteristic which can be selected or screened for. Libraries of recombinant polynucleotides are generated from a population of related-sequence polynucleotides which comprise sequence regions which have substantial sequence identity and can be homologous recombined in vitro or in vivo. In the method, at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide. Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein. The population of sequence-recombined polynucleotides comprises a subpopulation of polynucleotides which possess desired or advantageous characteristics and which can be selected by a suitable selection or screening method. The selected sequence-recombined polynucleotides, which are typically related-sequence polynucleotides, can then be subjected to at least one recursive cycle wherein at least one selected sequence-recombined polynucleotide is combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing desired characteristics. Such characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property.

Nucleic acid sequence shuffling is a method for recursive in vitro or in vivo homologous or nonhomologous recombination of pools of nucleic acid fragments or polynucleotides (e.g., genes from agricultural organisms or portions thereof). Mixtures of related nucleic acid sequences or polynucleotides are randomly or pseudo randomly fragmented, and reassembled to yield a library or mixed population of recombinant nucleic acid molecules or polynucleotides.

The present invention is directed to a method for generating a selected polynucleotide sequence (e.g., a plant ADPGPP gene or microbe ADPGPP gene, or combinations thereof) or population of selected polynucleotide sequences, typically in the form of amplified and/or cloned polynucleotides, whereby the selected polynucleotide sequence(s) possess a desired phenotypic characteristic of ADPGPP enzymes or subunits thereof which can be selected for, and whereby the selected polynucleotide sequences are genetic sequences having a desired functionality and/or conferring a desired phenotypic property to an agricultural organism in which the polynucleotide has been transferred into.

In a general aspect, the invention provides a method, called "sequence shuffling", for generating libraries of recombinant polynucleotides having a subpopulation of library members which encode an enhanced or improved ADPGPP L or S protein. Libraries of recombinant polynucleotides are generated from a population of related-sequence ADPGPP polynucleotides which comprise sequence regions which have substantial sequence identity and can be homologous recombined in vitro or in vivo. In the method, at least two species of the related-sequence ADPGPP polynucleotides are combined in a recombination system suitable for generating sequence-recombined polynucleotides, wherein said sequence-recombined polynucleotides comprise a portion of at least one first species of a related-sequence ADPGPP polynucleotide with at least one adjacent portion of at least one second species of a related-sequence ADPGPP polynucleotide. Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein, or template-switching of a retroviral genome replication event. The population of sequence-recombined polynucleotides comprises a subpopulation of ADPGPP polynucleotides which possess desired or advantageous enzymatic characteristics and which can be selected by a suitable selection or screening method. The selected sequence-recombined ADPGPP polynucleotides, which are typically related-sequence polynucleotides, can then be subjected to at least one recursive cycle wherein at least one selected sequence-recombined ADPGPP polynucleotide is combined with at least one distinct species of related-sequence ADPGPP polynucleotide (which may itself be a selected sequence-recombined polynucleotide) in a recombination system suitable for generating sequence-recombined ADPGPP polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing desired ADPGPP enzymatic characteristics. Such characteristics can be any property or attribute capable of being selected for or detected in a screening system.

Screening/selection produces a subpopulation of genetic sequences (or cells) expressing recombinant forms of ADPGPP subunit gene(s) that have evolved toward acquisition of a desired enzymatic property. These recombinant forms can then be subjected to further rounds of recombination and screening/selection in any order. For example, a second round of screening/selection can be performed analogous to the first resulting in greater enrichment for genes having evolved toward acquisition of the desired enzymatic property. Optionally, the stringency of selection can be increased between rounds (e.g., if selecting for drug resistance, the concentration of drug in the media can be increased). Further rounds of recombination can also be performed by an analogous strategy to the first round generating further recombinant forms of the gene(s) or genome(s). Alternatively, further rounds of recombination can be performed by any of the other molecular breeding formats discussed. Eventually, a recombinant form of the ADPGPP subunit gene(s) is generated that has fully acquired the desired enzymatic property.

In an embodiment, the first plurality of selected library members is fragmented and homologous recombined by PCR in vitro. Fragment generation is by nuclease digestion, partial extension PCR amplification, PCR stuttering, or other suitable fragmenting means, such as described herein and in WO 95/22625 published Aug. 24, 1995, and in commonly owned U.S. Ser. No. 08/621,859 filed Mar. 25, 1996, PCT/US96/05480 filed Apr. 18, 1996, which are incorporated herein by reference). Stuttering is fragmentation by incomplete polymerase extension of templates. A recombination format based on very short PCR extension times can be employed to create partial PCR products, which continue to extend off a different template in the next (and subsequent) cycle(s), and effect de facto fragmentation. Template-switching and other formats which accomplish sequence shuffling between a plurality of sequence-related polynucleotides can be used. Such alternative formats will be apparent to those skilled in the art.

In an embodiment, the first plurality of selected library members is fragmented in vitro, the resultant fragments transferred into a host cell or organism and homologous recombined to form shuffled library members in vivo.

In an embodiment, the first plurality of selected library members is cloned or amplified on episomally replicable vectors, a multiplicity of said vectors is transferred into a cell and homologous recombined to form shuffled library members in vivo.

In an embodiment, the first plurality of selected library members is not fragmented, but is cloned or amplified on an episomally replicable vector as a direct repeat or indirect (or inverted) repeat, which each repeat comprising a distinct species of selected library member sequence, said vector is transferred into a cell and homologous recombined by intra-vector or inter-vector recombination to form shuffled library members in vivo.

In an embodiment, combinations of in vitro and in vivo shuffling are provided to enhance combinatorial diversity. The recombination cycles (in vitro or in vivo) can be performed in any order desired by the practitioner.

In one embodiment, the first plurality of selected library members is fragmented and homologous recombined by PCR in vitro. Fragment generation is by nuclease digestion, partial extension PCR amplification, PCR stuttering, or other suitable fragmenting means, such as described herein and in the documents incorporated herein by reference. Stuttering is fragmentation by incomplete polymerase extension of templates.

In one embodiment, the first plurality of selected library members is fragmented in vitro, the resultant fragments transferred into a host cell or organism and homologous recombined to form shuffled library members in vivo. In an aspect, the host cell is a plant cell which has been engineered to contain enhanced recombination systems, such as an enhanced system for general homologous recombination (e.g., a plant expressing a recA protein or a plant recombinase from a transgene or plant virus) or a site-specific recombination system (e.g., a cre/LOX or frt/FLP system encoded on a transgene or plant virus).

In one embodiment, the first plurality of selected library members is cloned or amplified on episomally replicable vectors, a multiplicity of said vectors is transferred into a cell and homologous recombined to form shuffled library members in vivo in a plant cell, algae cell, or bacterial cell. Other cell types may be used, if desired.

In one embodiment, the first plurality of selected library members is not fragmented, but is cloned or amplified on an episomally replicable vector as a direct repeat or indirect (or inverted) repeat, which each repeat comprising a distinct species of selected library member sequence, said vector is transferred into a cell and homologous recombined by intra-vector or inter-vector recombination to form shuffled library members in vivo in a plant cell, algae cell, or microorganism.

In an embodiment, combinations of in vitro and in vivo shuffling are provided to enhance combinatorial diversity.

At least two additional related specific formats are useful in the practice of the present invention. The first, referred to as "in silico" shuffling utilizes computer algorithms to perform "virtual" shuffling using genetic operators in a computer. As applied to the present invention, ADPGPP nucleic acid (or protein) sequence strings are recombined in a computer system and desirable products are made, e.g., by reassembly PCR or ligation of synthetic oligonucleotides, or other available techniques. In silico shuffling is described in detail in Selifonov and Stemmer in "METHODS FOR MAKING CHARACTER STRINGS, POLYNUCLEOTIDES & POLYPEPTIDES HAVING DESIRED CHARACTERISTICS" filed Feb. 15, 1996, U.S. Ser. No. 60/118854 and "METHODS FOR MAKING CHARACTER STRINGS, POLYNUCLEOTIDES & POLYPEPTIDES HAVING DESIRED CHARACTERISTICS" by Selifonov et al. filed Oct. 12, 1999 (U.S. Ser. No.09/416375). In brief, genetic operators (algorithms which represent given genetic events such as point mutations, recombination of two strands of homologous nucleic acids, etc.) are used to model recombinational or mutational events which can occur in one or more nucleic acid, e.g., by aligning nucleic acid sequence strings (using standard alignment software, or by manual inspection and alignment) and predicting recombinational outcomes based upon selected genetic algorithms (mutation, recombination, etc.). The predicted recombinational outcomes are used to produce corresponding molecules, e.g., by oligonucleotide synthesis and reassembly PCR. As applied to the present invention, ADPGPP nucleic acids are aligned and recombined in silico, using any desired genetic operator, to produce character strings which are then generated synthetically for subsequent screening.

The second useful format is referred to as "oligonucleotide mediated shuffling" in which oligonucleotides corresponding to a family of related homologous nucleic acids (e.g., as applied to the present invention, families of homologous ADGPP variants of a nucleic acid) which are recombined to produce selectable nucleic acids. This format is described in detail in Crameri et al. "OLIGONUCLEOTIDE MEDIATED NUCLEIC ACID RECOMBINATION" filed Feb. 5, 1999, U.S. Ser. No. 60/118,813, Crameri et al. "OLIGONUCLEOTIDE MEDIATED NUCLEIC ACID RECOMBINATION" filed Jun. 24, 1999, U.S. Ser. No. 60/141,049; Crameri et al. "OLIGONUCLEOTIDE MEDIATED NUCLEIC ACID RECOMBINATION" filed Sep. 28, 1999 (U.S. Ser. No. 09/408,392, and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393. In brief, selected oligonucleotides corresponding to multiple homologous parental nucleic acids are synthesized, ligated and elongated (typically in a recursive format), typically either in a polymerase or ligase-mediated elongation reaction, to produce full-length ADPGPP nucleic acids. The technique can be used to recombine homologous or even nonhomologous ADPGPP nucleic acid sequences.

One advantage of oligonuclcotide-mediated recombination is the ability to recombine homologous nucleic acids with low sequence similarity, or even non-homologous nucleic acids. In these low-homology oligonucleotide shuffling methods, one or more set of fragmented nucleic acids (e.g., oligonucleotides corresponding to multiple ADPGPP nucleic acids) are recombined, e.g., with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived by comparison to one or more homologous or non-homologous nucleic acids, can hybridize to one or more region of the crossover oligos, facilitating recombination.

When recombining homologous nucleic acids, sets of overlapping family gene shuffling oligonucleotides (which are derived by comparison of homologous nucleic acids, by synthesis of corresponding oligonucleotides) are hybridized and elongated (e.g., by reassembly PCR or ligation), providing a population of recombined nucleic acids, which can be selected for a desired trait or property. The set of overlapping family shuffling gene oligonucleotides includes a plurality of oligonucleotide member types which have consensus region subsequences derived from a plurality of homologous target nucleic acids.

Typically, as applied to the present invention, family gene shuffling oligonucleotides which include one or more ADPGPP nucleic acid(s) are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity.

Sets of fragments, or subsets of fragments used in oligonucleotide shuffling approaches can be provided by cleaving one or more homologous nucleic acids (e.g., with a DNase), or, more commonly, by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments can be used in conjunction with family gene shuffling oligonucleotides, e.g., in one or more recombination reaction to produce recombinant ADPGPP nucleic acid(s).

One final synthetic variant worth noting is found in "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, PCT/US99/22588. As noted in detail in this set of related applications, one way of generating diversity in a set of nucleic acids to be shuffled (i.e., as applied to the present invention, ADPGPP nucleic acids), is to provide codon-altered nucleic acids which can be shuffled to provide access to sequence space not present in naturally occurring sequences. In brief, by synthesizing nucleic acids in which the codons which encode polypeptides are altered, it is possible to access a completely different mutational spectrum upon subsequent mutation of the nucleic acid. This increases the sequence diversity of the starting nucleic acids for shuffling protocols, which alters the rate and results of forced evolution procedures. Codon modification procedures can be used to modify any ADGPP nucleic acid or shuffled nucleic acid, e.g., prior to performing DNA shuffling.

In brief, oligonucleotide sets comprising codon variations are synthesized and reassembled into full-length nucleic acids. The full length nucleic acids can themselves be shuffled (e.g., where the oligonucleotides to be reassembled provide sequence diversity at selected sites), and/or the full-length sequences can be shuffled by any available procedure to produce diverse sets of ADGPP nucleic acids.

Improved Plants

Without reciting the various generalized formats of polynucleotide sequence shuffling and selection described previously or hereinbelow, which will be referred to herein by the shorthand "shuffling", the present invention provides methods, compositions, and uses related to creating novel or improved plants, plant cells, algal cells, soil microbes, plant pathogens, commensal microbes, or other plant-related organisms having art-recognized importance to the agricultural, horticultural, and argonomic areas (collectively, "agricultural organisms").

For example, agronomically and horticulturally important plant species can be transduced. Such species include, but are not restricted to, members of the families: Graminae (including corn, rye, triticale, barley, millet, rice, wheat, oats, etc.); Leguminosae (including pea, beans, lentil, peanut, yam bean, cowpeas, velvet beans, soybean, clover, alfalfa, lupine, vetch, lotus, sweet clover, wisteria, and sweetpea); Compositae (the largest family of vascular plants, including at least 1,000 genera, including important commercial crops such as sunflower) and Rosaciae (including raspberry, apricot, almond, peach, rose, etc.), as well as nut plants (including, walnut, pecan, hazelnut, etc.).

Additionally, preferred targets include plants from the genera: Agrostis, Allium, Antirrhinum, Apium, Arachis, Asparagus, Atropa, Avena (e.g., oats), Barnbusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthius, Heterocallis, Hevea, Hordeum (e.g., barley), Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza (e.g., rice), Panicumn, Pelargonium, Pennisetum (e.g., millet), Petunia, Pisum, Phaseolus, Phleum, Poa, Prunus, Ranunculus, Raphanus, Ribes, Ricinus, Rubus, Saccharum, Salpiglossis, Secale (e.g., rye), Senecio, Setaria, Sinapis, Solanum, Sorghum, Stenotaphrum, Theobroma, Trifolium, Trigonella, Triticum (e.g., wheat), Vicia, Vigna, Vitis, Zea (e.g., corr,), the Olyreae, the Pharoideae and many others.

For example, common crop plants which are targets of the present invention include corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea and nut plants (e.g., walnut, pecan, etc).

In certain variations, naturally occurring in vivo recombination mechanisms of plants, agricultural microorganisms, or vector-host cells for intermediate replication can be used in conjunction with a collection of shuffled polynucleotide sequence variants having a desired phenotypic property to be optimized further; in this way, a natural recombination mechanism can be combined with intelligent selection of variants in an iterative manner to produce optimized variants by "forced evolution", wherein the forced evolved variants are not expected to, nor are observed to, occur in nature, nor are predicted to occur at an appreciable frequency. The practitioner may further elect to supplement and/or the mutational drift by introducing intentionally mutated polynucleotide species suitable for shuffling, or portions thereof, into the pool of initial polynucleotide species and/or into the plurality of selected, shuffled polynucleotide species which are to be recombined. Mutational drift may also be supplemented by the use of mutagens (e.g., chemical mutagens or mutagenic irradiation), or by employing replication conditions which enhance the mutation rate.

Forced Evolution of Genes

The invention provides a means to evolve ADPGPP (S and/or L) gene variants and/or suitable host cells, as well as providing a model system for evaluating a library of agents to identify candidate agents that could find use as agricultural reagents for commercial applications. Such agents may exhibit selectivity for inhibition of a naturally occurring ADPGPP enzyme and may be substantially less effective at inhibiting a shuffled ADPGPP enzyme which has been evolved to be resistant to the agent.

ADPGPP Shuffling Combinations

Although the skilled artisan may select alternative shuffling strategies for enhancing ADPGPP enzyme properties, the following general combinations can be used:

1. Shuffling an ADPGPP from a First Species of Bacteria with an ADPGPP from a Second Species of Bacteria. The resultant shufflants may be transformed into bacterial host cells which preferably lack endogenous ADPGPP activity (e.g., *E coli* mutants glgC), algal cells, or plant cells for expression and selection. Phenotype selection of shufflants is typically performed by biochemical assay for ADPGPP, such as according to Preiss et al. (1966) *Biochemistry* 5: 1833; or other suitable assay method selected by the artisan, including microscopic detection of starch granules, specific gravity, iodine vapor colorimetry, or the like. Example bacteria for obtaining the ADPGPP gene(s) include *Rhodobacter sphaeroides, Rhodospirrilum rubrum, Escherichia coli, Salmonella typhimurium*, and the like. A preferred host cell is a strain of bacterium that is transformable and which lacks ADPGPP activity (e.g., glgC mutant of *E coli* ).

II. Shuffling a Parental Bacterial ADPGPP Encoding Sequence with Mutagenized Variants Thereof: The resultant shufflants may be transformed into bacterial host cells which preferably lack endogenous ADPGPP activity (e.g., *E coli* ), algal cells, or plant cells for expression and selection. Phenotype selection of shufflants is typically performed by biochemical assay for ADPGPP activity or other suitable assay method selected by the artisan.

III. Shuffling a L or S Subunit from a First Species of Plant with a L Subunit from a Non-plant Algae or Bacterium, Cyanobacteria. The resultant shufflants may be transformed into host cells which preferably lack endogenous ADPGPP activity (e.g., *E coli* ), algal cells, or plant cells for expression and selection. Phenotype selection of shufflants is typically performed by biochemical assay for ADPGPP or other suitable assay method selected by the artisan. Example bacteria for the ADPGPP gene(s) include Rhodobacter sphaeroides (Falcone et al. (1998) *J. Bact.* 170: 5), *Rhodospirrilum rubrum* (Falcone and Tabita (1993) *J.Bact*. 175: 5066; Falcone et al. (1991) J. Bact. 173: 2099), *Escherichia coli, Salmonella typhimurium*, and the like. Example cyanobacteria that can serve as a source of ADPGPP genes include Synechococcus, *Cocochloris peniocystis*, and *Aphanizomenon flos-aquae*. Example green algae that can serve as sources of ADPGPP genes include *Euglena gracilis, Chlamadomonas reinhardii*, and *Anacystis nidulans*. Example plants that can serve as sources for the L or S subunit genes include rice, maize, potato, wheat, rye, flax, cotton, pea, and the like.

IV. Shuffling a Plant L Subunit from a First Plant Taxonomic Species with a Plant L Subunit from a Second Plant Taxonomic Species. The resultant shufflants may be transformed into host cells, which can preferably lack endogenous ADPGPP activity, but which fold and process higher plant ADPGPP subunits correctly for expression and selection, and generally encode and express a complementing plant S subunit, often encoded by a sequence derived from one or both of the higher plant species. Phenotype selection of shufflants is typically performed by iodine vapor visualization of blue-stained cells or by biochemical assay for ADPGPP or other suitable assay method selected by the artisan. Example higher plants that can serve as a source of ADPGPP L genes include, but are not limited to: *Zea mays* (C4), *Amaranthus hybridus* (C4), *glycine max* (C3), and *Nicotiana tabacum* (C3).

V. Shuffling a plant S Subunit from a First Plant Taxonomic Species with a Plant S Subunit from a Second Plant Taxonomic Species. The resultant shufflants may be transformed into host cells, which can preferably lack endogenous ADPGPP activity, but which fold and process higher plant ADPGPP subunits correctly for expression and selection, and generally encode and express a complementing plant L subunit, often encoded by a sequence derived from one or both of the higher plant species. Phenotype selection of shufflants is typically performed by iodine vapor visualization of blue-stained cells or by biochemical assay for ADPGPP or other suitable assay method selected by the artisan. Example higher plants that can serve as a source of ADPGPP S genes include, but are not limited to: *Zea mays* (C4), *Amaranthus hybridus* (C4), *glycine max* (C3), and *Nicotiana tabacum* (C3).

VI. Shuffling a L or S Subunit from a Higher Plant with Mutagenized Variants Thereof. An ADPGPP L or S gene ("parental gene") from a species of C3 or C4 plant is subjected to mutagenesis and shuffling/selection to generate a population of mutagenized shufflants which have substantial sequence identity to the parental gene. The population of mutagenized shufflants is transferred into a population of host cells wherein the mutagenized shufflants are expressed and the resultant transformed host cell population is selected or screened for an enhanced ADPGPP phenotype. Phenotype selection of shufflants is typically performed by biochemical assay for ADPGPP activity or other suitable assay method selected by the artisan.

Transcriptional Regulatory Sequences

Suitable transcriptional regulatory sequences include: cauliflower mosaic virus 19S and 35S promoters, NOS promoter, OCS promoter, rbcS promoter, Brassica heat shock promoter, synthetic promoters, non-plant promoters modified, if necessary, for function in plant cells, substantially any promoter that naturally occurs in a plant genome, promoters of plant viruses or Ti plasmids, tissue-preferential promoters or cis-acting elements, light-responsive promoters or cis-acting elements (e.g., rbcS LRE), hormone-responsive cis-acting elements, developmental stage-specific promoters, organ specific promoters, cis-acting elements for promoters, viral promoters (e.g., from Tobacco Mosaic virus, Brome Mosaic Virus, Cauliflower Mosaic virus, and the like), and the like. In a variation, a transcriptional regulatory sequence from a first plant species is optimized for functionality in a second plant species by application of recursive sequence shuffling.

Transcriptional regulatory sequences for expression of shuffled ADPGPP sequences in chloroplasts are known in the art (Daniell et al. (1998) op.cit; O'Neill et al. (1993) *The Plant Journal* 3: 729; Maliga P (1993) op.cit), as are homologous recombination vectors.

Host Cells for Screening ADPGPP Gene Shufflants

A variety of suitable host cells will be apparent to those skilled in the art. Of particular note, ADPGPP gene shufflants can be expressed in the glgC deletion mutant strain of *E coli*, as well as higher taxonomic host cells. However, subunits from higher plants may not be processed correctly in bacterial host cells, so higher plant L and S gene shufflants may often be expressed for phenotype screening in plant cells, including mutant plant cell lines wherein an endogenous ADPGPP encoding gene has been functionally inactivated, preferably in homozygous format, to provide a plant cell substantially lacking endogenous ADPGPP activity, or the like.

Transformation

The transformation of plants and protoplasts in accordance with the invention may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press, incorporated herein by reference. As used herein, the term transformation means alteration of the genotype of a host plant by the introduction of a nucleic acid sequence. The nucleic acid sequence need not necessarily originate from a different source, but it will, at some point, have been external to the cell into which it is to be introduced.

In one embodiment, the foreign nucleic acid is mechanically transferred by microinjection directly into plant cells by use of micropipettes. Alternatively, the foreign nucleic acid may be transferred into the plant cell by using polyethylene glycol. This forms a precipitation complex with the genetic material that is taken up by the cell (e.g., by incubation of protoplasts with "naked DNA" in the presence of polyethylenelycol)(Paszkowski et al., (1984) *EMBO J.*3:2717–22; Baker et al (1985) Plant Genetics, 201–211; Li et al. (1990) Plant Molecular Biology Report 8 (4)276–291].

In another embodiment of this invention, the introduced gene may be introduced into the plant cells by electroporation (Fromm et al., (1985) "Expression of Genes Transferred into Monocot and Dicot Plant Cells by Electroporation," *Proc. Natl Acad. Sci. USA* 82:5824, which is incorporated herein by reference). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) may also be used as a vector for introducing the foreign nucleic acid into plant cells (Hohn et al., (1982) "Molecular Biology of Plant Tumors," Academic Press, New York, pp.549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of nucleic acid segments is high velocity ballistic penetration by small particles with the nucleic acid either within the matrix of small beads or particles, or on the surface (Klein et al., (1987) *Nature* 327:70–73). Although typically only a single introduction of a new nucleic acid segment is required, this method particularly provides for multiple introductions.

A method of introducing the nucleic acid segments into plant cells is to infect a plant cell, an explant, a meristem or a seed with *Airobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," *Science*, 233:496–498; Fraley et al., (1983) *Proc. Nati. Acad. Sci. USA* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector."

All plant cells which can be transformed by Agrobacterium and whole plants regenerated from the transformed cells can also be transformed according to ZX) the invention so as to produce transformed whole plants which contain the transferred foreign nucleic acid sequence.

There are presently at least three different ways to transform plant cells with Agrobacterium: (1) co-cultivation of Agrobacterium with cultured isolated protoplasts; (2) transformation of cells or tissues with Agrobacterium, or (3) transformation of seeds, apices or meristems with Agrobacterium .

Method (1) uses an established culture system that allows culturing protoplasts and plant regeneration from cultured protoplasts.

Method (2) implies (a) that the plant cells or tissues can be transformed by Agrobacterium and (b) that the transformed cells or tissues can be induced to regenerate into whole plants.

Method (3) uses micropropagation. In the binary system, to have infection, two plasmids are needed: a T-DNA containing plasmid and a vir plasmid. Any one of a number of T-DNA containing plasmids can be used, the main issue being that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

Protoplast Transformation

Numerous protocols for establishment of transformable protoplasts from a variety of plant types and subsequent transformation of the cultured protoplasts are available in the art and are incorporated herein by general reference. For examples, see Hashimoto et al. (1990) *Plant Physiol.* 93: 857; *Plant Protoplasts*, Fowke LC and Constabel F, eds., CRC Press (1994); Saunders et al. (1993) Applications of Plant In Vitro Technology Symposium, UPM, 16–18 Nov. 1993; and Lyznik et al. (1991) *BioTechnigues* 10: 295, each of which is incorporated herein by reference).

All plants from which protoplasts can be isolated and cultured to give whole regenerated plants can be transformed by the present invention so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelarionium, Panicum, Pennisetum, Ranunculus, Senecio, Salpiglossis, Cucumis, Browaalia, Glycine, Lolium, Zea, Triticum, Sorghum, and Datura.

It is known that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Although monocotyledonous plants, and in particular, cereals and grasses, are not natural hosts to Aigrobacterium, work to transform them using Agrobacterium has also been successfully carried out by numerous investigators (Hooykas-Van Slogteren et al., (1984) *Nature* 311:763–764; Hemalsteens et al., (1984) *EMBO J.* 3:3039–41; Byteiber, et al. (1987) *Proc. Natl. Acad. Sci. USA:* 5345–5349; Graves and Goldman, (1986) *Plant Mol. Biol* 7: 43–50; Grimsley et al. (1988) *Biochemistry* 6: 185–189; WO 86/03776; Shimamoto et al. *Nature* (1989) 338: 274–276). Monocots may also be transformed by techniques or with vectors other than Agrobacterium. For example, monocots have been transformed by electroporation (Fromm et al. [1986] *Nature* 319:791–793; Rhodes et al. *Science* [1988] 240: 204–207), direct gene transfer (Baker et al. [1985] *Plant Genetics* 201–211), by using pollen-mediated vectors (EP 0 270 356), and by injection of DNA into floral tillers (de la Pena et al. [1987], *Nature* 325:274–276). Additional plant genera that may be transformed by Agrobacterium include Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus and Pisum. Chloroplast Transformation As the ADPGPP enzyme of higher plants is encoded in the nuclear genome and expressed with a fused chloroplast transit sequence peptide (CTS) to facilitate transloaction of the ADPGPP subunits into chloroplasts, it can be advantageous to transform the shufflant ADPGPP encoding sequences into chloroplasts if the host cells are derived from higher plants. Numerous methods are available in the art to accomplish the chloroplast transformation and expression (Daniell et al. (1998) op.cit; O'Neill et al. (1993) *The Plant Journal* 3: 729; Maliga P (1993) op.cit). The expression construct comprises a transcriptional regulatory sequence functional in plants operably linked to a polynucleotide encoding an enhanced ADPGPP protein subunit. With respect to polynucleotide sequences encoding ADPGPP subunit proteins, it may be desirable to express such encoding sequences in plastids, such as chloroplasts, for appropriate transcription, translation, and processing. With reference to expression cassettes which are designed to function in chloroplasts, such as an expression cassette encoding a subunit of ADPGPP in a higher plant, the expression cassette comprises the sequences necessary to ensure expression in chloroplasts—typically the subunit encoding sequence is flanked by two regions of homology to the plastid genome so as to effect a homologous recombination with the chloroplastid genome; often a selectable marker gene is also present within the flanking plastid DNA sequences to facilitate selection of genetically stable transformed chloroplasts in the resultant transplastonic plant cells (see Maliga P (1993) *TIBTECH* 11 101; Daniell et al. (1998) *Nature Biotechnology* 16: 346, and references cited therein).

Recovery of Selected Polynucleotide Sequences

A variety of selection and screening methods will be apparent to those skilled in the art, and will depend upon the particular phenotypic properties that are desired. The selected shuffled genetic sequences can be recovered for further shuffling or for direct use by any applicable method, including but not limited to: recovery of DNA, RNA, or cDNA from cells (or PCR-amplified copies thereof) from cells or medium, recovery of sequences from host chromosomal DNA or PCR-amplified copies thereof, recovery of episome (e.g., expression vector plasmid, cosmid, viral vector, artificial chromosome, and the like, or other suitable recovery method known in the art.

Any suitable art-known method, including RT-PCR or PCR, can be used to obtain the selected shufflant sequence(s) for subsequent manipulation and shuffling.

Backcrossing

After a desired ADPGPP phenotype is acquired to a satisfactory extent by a selected shuffled gene or portion thereof, it is often desirable to remove mutations which are not essential or substantially important to retention of the desired phenotype ("superfluous mutations"). This is particularly desirable when the shuffled gene sequence is to be reintroduced back into a higher plant, as it is often preferred to harmonize the shufflant ADPGPP subunit sequence with the endogenous ADPGPP subunit sequence in the higher plant taxonomic species genome while retaining the desired ADPGPP phenotype obtained from the iterative shuffling/selection process. Superfluous mutations can be removed by backcrossing, which is shuffling the selected shuffled ADPGPP L gene(s) with one or more parental ADPGPP L gene and/or naturally-occurring ADPGPP L gene(s) (or portions thereof) and selecting the resultant collection of shufflants for those species that retain the desired phenotype. The same process may be employed for the ADPGPP S genes. By employing this method, typically in two or more recursive cycles of shuffling against parental or naturally-occurring viral genome(s) (or portions thereof) and selection for retention of the desired ADPGPP phenotype, it is possible to generate and isolate selected shufflants which incorporate substantially only those mutations necessary to confer the desired phenotype, whilst having the remainder of the genome (or portion thereof) consist of sequence which is substantially identical to the parental (or wild-type) sequence(s). As one example of backcrossing, a potato ADPGPP subunit gene (small or large subunit) can be shuffled and selected for the capacity to substantially function in any Angiosperm plant cells; the resultant selected shufflants can be backcrossed with one or more ADPGPP genes of a particular plant species and selected for the capacity to retain the capacity to confer the phenotype. After several cycles of such backcrossing, the backcrossing will yield gene(s) which contain the mutations necessary for the desired phenotype, and will otherwise have a genomic sequence substantially identical to the genome(s) of the host genome.

Isolated components (e.g., genes, regulatory sequences, replication origins, and the like) can be optimized and then backcrossed with parental sequences so as to obtain optimized components which are substantially free of superfluous mutations.

Transgenic Hosts

Transgenes and expression vectors to express shufflant ADPGPP sequences can be constructed by any suitable method known in the art; by either PCR or RT-PCR amplification from a suitable cell type or by ligating or amplifying a set of overlapping synthetic oligonucleotides; publicly available sequence databases and the literature can be used to select the polynucleotide sequence(s) to encode the specific protein desired, including any mutations, consensus sequence, or mutation kernel desired by the practitioner. The coding sequence(s) are operably linked to a transcriptional regulatory sequence and, if desired, an origin of replication. Antisense or sense-suppression transgenes and genetic sequences can be optimized or adapted for particular host cells and organisms by the described methods.

The transgene(s) and/or expression vectors are transferred into host cells, protoplasts, pluripotent embryonic plant cells, microbes, or fungi by a suitable method, such as for example lipofection, electroporation, microinjection, biolistics, *Agrobacterium tumefaciens* transduction of Ti plasmid, calcium phosphate precipitation, PEG-mediated DNA uptake, electroporation, electrofusion, or other method. Stable transfectant host cells can be prepared by art-known methods, as can transgenic cell lines.

Target Plants

As used herein, "plant" refers to either a whole plant, a plant part, a plant cell, or a group of plant cells. The class of plants which can be used in the method of the invention is generally as broad as the class of higher plants amenable to protoplast transformation techniques, including both monocotyledonous and dicotyledonous plants. It includes plants of a variety of ploidy levels, including polyploid, diploid and haploid, and may employ non-regenerable cells for certain aspects which do not require development of an adult plant for selection or in vivo shuffling.

Preferred plants for the transformation and expression shuffled genes of this invention include agronomically and horticulturally important species. Such species include, but are not restricted to members of the families: Graminae (including corn, rye, triticale, barley, millet, rice, wheat, oats, etc.); Leguminosae (including pea, beans, lentil, peanut, yam bean, cowpeas, velvet beans, soybean, clover, alfalfa, lupine, vetch, lotus, sweet clover, wisteria, and sweetpea); Compositae (the largest family of vascular plants, including at least 1,000 genera, including important commercial crops such as sunflower) and Rosaciae (including raspberry, apricot, almond, peach, rose, etc.), as well as nut plants (including, walnut, pecan, hazelnut, etc.)

Targets for the invention include plants from the genera: Agrostis, Allium, Antirrhinum, Apium, Arachis, Asparagus, Atropa, Avena (e.g., oats), Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum (e.g., barley), Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza (e.g., rice), Panicum, Pelargonium, Pennisetum (e.g., millet), Petunia, Pisum, Phaseolus, Phleum, Poa, Prunus, Ranunculus, Raphanus, Ribes, Ricinus, Rubus, Saccharum, Salpiglossis, Secale (e.g., rye), Senecio, Setaria, Sinapis, Solanum, Sorghum, Stenotaphrum, Theobroma, Trifolium, Trigonella, Triticum (e.g., wheat), Vicia, Vigna, Vitis, Zea (e.g., corn), and the Olyreae, the Pharoideae and many others.

Common crop plants which are targets of the present invention include corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea and nut plants (e.g., walnut, pecan, etc).

Regeneration

Normally, regeneration will be involved in obtaining a whole plant from the transformation process. The term "transgenote" refers to the immediate product of the transformation process and to resultant whole transgenic plants.

The term "regeneration" as used herein, means growing a whole plant from a plant cell, a group of plant cells, a plant part or a plant piece (e.g. from a protoplast, callus, or tissue part).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," Protoplasts, (1983)—Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)—Lecture Proceedings, pp. 31–41, (Birkhauser, Basel 1983); and H. Binding, "Regeneration of Plants," *Plant Protoplasts*, pp.21–73, (CRC Press, Boca Raton 1985).

Additional details regarding plant regeneration are found in Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); Gamborg and Phillips (eds) (1995) *Plant Cell. Tissue and Organ Culture, Fundamental Methods* Springer Lab Manual, Springer-Verlag (Berlin Heidelberg N.Y.) (Gamborg) and in Croy, (ed.) (1993) *Plant Molecular Biology.*

Regeneration from protoplasts varies from species to species of plants, but generally a suspension of transformed protoplasts containing copies of the exogenous sequence is first made. In certain species embryo formation can then be induced from the protoplast suspension, to the stage of ripening and germination as natural embryos. The culture media will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is filly reproducible and repeatable.

Regeneration also occurs from plant callus, explants, organs or parts. Transformation can be performed in the context of organ or plant part regeneration. See, *Methods in Enzymology*, supra; also *Methods in Enzymology*, Vol. 118; and Klee et al., (1987) *Annual Review of Plant Physiology*, 38:467–486.

In vegetatively propagated crops, the mature transgenic plants are propagated by the taking of cuttings or by tissue culture techniques to produce multiple identical plants for trialling, such as testing for production characteristics. Selection of desirable transgenotes is made and new varieties are obtained thereby, and propagated vegetatively for commercial sale.

In seed propagated crops, the mature transgenic plants are self crossed to produce a homozygous inbred plant. The inbred plant produces seed containing the gene for the newly introduced foreign gene activity level. These seeds can be grown to produce plants that would produce the selected phenotype.

The inbreds according to this invention can be used to develop new hybrids. In this method a selected inbred line is crossed with another inbred line to produce the hybrid. The offspring resulting from the first experimental crossing of two parents is known in the art as the F1 hybrid, or first filial generation. Of the two parents crossed to produce F I progeny according to the present invention, one or both parents can be transgenic plants.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

The following example is given to illustrate the invention, but are not to be limiting thereof.

EXPERIMENTAL EXAMPLE

EXAMPLE 1

Shuffling ADP-glucose Pyrophosphorylase

Genes coding for ADP-glucose pyrophosphorylase (ADPGPP) from *E. coli* are isolated using primers designed from published sequence in the Genbank. A genomic DNA library of *E coli* is used as a source for the ADPGPP gene. Similarly, ADPGPP genes from other microorganisms are isolated including from cyanobacteria. All of these prokaryotes have a single subunit ADPGPP (Preiss J, (1996) *Biotechnology Annual Review* Vol. 2, pp259–279).

The ADPGPP genes from various microorganisms, which have at least 70 percent nucleotide sequence identity are shuffled according to published procedures. Briefly, this procedure involves random fragmentation of the genes with DNAse I and selecting nucleotide fragments of 100–300 bp. The fragments are reassembled based on sequence similarity by primerless PCR. Recombination as well as variable levels of mutations that are introduced by the PCR reaction generate the diversity. The assembled genes is cloned into a starch minus *E. coli* mutant that lacks ADPGPP such as LCB618 (available at the *Coli* Genetics Stock Center at Yale). Transformed colonies expressing a functional ADPGPP are screened for production of glycogen by iodine staining (Greene TW et al. (1996) *PNAS* 93: 1509–1513). Those colonies staining dark blue (greater starch content) are presumed to contain deregulated ADPGPP. Colonies expressing shuffled ADPGPP genes are selected and grown in larger amounts in liquid culture and assayed for specific properties (Meyer et al. (1998) *Archives Biochem. Biophys.* Pp152–159) relative to the wildtype enzyme, such as: (a) insensitivity to activation by fructose-1, 6-bisphosphate (FBP) (b) desensitized to inhibition by AMP and inorganic phosphate (c) decreased Km for the two substrates, glucose-1-phosphate and ATP (d) increased Vmax. Genes from those clones expressing one or more of the desired properties mentioned above are iteratively shuffled in order to achieve optimization of one or more of the properties mentioned above. The optimized gene, after appropriate modification, is used to transform the desired crop species in order to deregulate and increase starch biosynthesis in various tissues including tubers and seeds.

Plant genes coding for ADPGPP are cloned into *E coli* (Iglesias A et al. *J. Biol Chem* 268:1081–1086) and shuffled as described above, to optimize the desired properties. The plant enzyme is composed of two subunits, the small catalytic and the large regulatory subunit. Both genes are shuffled individually or in combination. Selection is done in *E coli* as described above. Enzyme assays can be performed for analysis of properties as described in literature (Meyer et al. (1998) *Archives Biochem. Biophys.* Pp152–159). A difference between the plant and bacterial enzyme is that the activator is 3-phosphoglycerate and the inhibitor is inorganic phosphate.

Integrated Systems

The present invention provides computers, computer readable media and integrated systems comprising character strings corresponding to shuffled ADPGPP enzyme and corresponding enzyme-encoding nucleic acids. These sequences can be manipulated by in silico shuffling methods, or by standard sequence alignment or word processing software.

For example, different types of similarity and considerations of various stringency and character string length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with algorithms for calculating sequence similarity is BLAST, which can be adapted to the present invention by inputting character strings corresponding to the sequences herein.

BLAST is described in Altschul et al., *J Mol Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J Mol. Evol.* 35:351–360 (1987). The method used is similar to the method described by Higgins & Sharp, *CABIOS* 5:151–153 (1989). The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

The shuffled enzymes of the invention, or corresponding coding nucleic acids, are optionally sequenced and the sequences aligned to provide structure-function information. For example, the alignment of shuffled sequences which are selected for conversion activity against the same target provides an indication of which residues are relevant for conversion of the target (i.e., conserved residues are likely more important for activity than non-conserved residues).

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting character strings corresponding to shuffled ADPGPP enzymes (or corresponding coding nucleic acids), e.g., shuffled by the methods herein. For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST or PILEUP can also be incorporated into the systems of the invention for alignment of nucleic acids or proteins (or corresponding character strings).

Integrated systems for analysis in the present invention typically include a digital computer with software for aligning or manipulating sequences, as well as data sets entered into the software system comprising any of the sequences herein. The computer can be, e.g., a PC (Intel x86 or Pentium chip- compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visual basic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operation.

In one aspect, the computer system is used to perform "in silico" shuffling of character strings. A variety of such methods are set forth in "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118854) and "METHODS FOR MAKING CHARACTER STRINGS, POLYNUCLEOTIDES & POLYPEPTIDES HAVING DESIRED CHARACTERISTICS" by Selifonov and Stemmer, filed Oct. 12, 1999 (U.S. Ser. No. 09/416,375). In brief, in the context of the present invention, genetic operators are used in genetic algorithms as described in the '375 application to change given ADPGPP sequences, e.g., by mimicking genetic events such as mutation, recombination, death and the like. Multi-dimensional analysis to optimize sequences can be also be performed in the computer system, e.g., as described in the '375 application.

A digital system can also instruct an oligonucleotide synthesizer to synthesize oligonucleotides, e.g., used for ADPGPP gene reconstruction or recombination, or to order oligonucleotides from commercial sources (e.g., by printing appropriate order forms or by linking to an order form on the internet).

The digital system can also include output elements for controlling nucleic acid synthesis (e.g., based upon a sequence or an alignment of a shuffled enzyme as herein), i.e., an integrated system of the invention optionally includes an oligonucleotide synthesizer or an oligonucleotide synthesis controller. The system can include other operations which occur downstream from an alignment or other operation performed using a character string corresponding to a sequence herein, e.g., as noted above with reference to assays.

Combination Shuffling

One aspect of the present inventions the combinatorial shuffling of ADGPP with enzymes that affect carbon fixation. For example, one aspect of the present invention involves separately or simultaneously shuffling AEGPP in combination with carbon fixation enzymes such as ribulose 1,5-bisphosphate carboxylase/oxygenase ("Rubisco"; EC 4.1.1.39), or with any Calvin cycle enzyme or Krebs cycle enzyme. Considerable detail regarding Rubisco and Calvin and Krebs cycle enzymes and shuffling of such enzymes to improve carbon fixation is found in commonly assigned U.S. patent application U.S. Ser. No. 60/107,756 and 60/153,093 entitled "MODIFIED RIBULOSE BISPHOSPHATE CARBOXYLASE/OXYGENASE FOR IMPROVEMENT AND OPTIMIZATION OF PLANT PHENOTYPES," filed on Nov. 10, 1998 and Sep. 9, 1999, respectively and in "MODIFIED RIBULOSE BISPHOSPHATE CARBOXYLASE/OXYGENASE FOR IMPROVEMENT AND OPTIMIZATION OF PLANT PHENOTYPES," by Stemmer et al., co-filed Nov. 9, 1999. Shuffled ADPGPP genes and shuffled Rubisco optionally co-expressed in a cell or organism such as a plant to increase starch production and carbon fixation.

Similarly, shuffled ADPGPP genes can be expressed with shuffled Phosphoenolpyruvate (PEP) carboxylase (PEPC; EC 4.1.1.31) genes to improve carbon fixation and starch production. Considerable detail regarding PEPC gene shuffling is found in commonly assigned U.S. patent application U.S. Ser. No. 60/107,757 entitled "MODIFIED PHOSPHOENOLPYRUVATE CARBOXYLASE FOR IMPROVEMENT AND OPTIMIZATION OF PLANT PHENOTYPES" filed on Nov. 10, 1998 and in "MODIFIED PHOSPHOENOLPYRUVATE CARBOXYLASE FOR IMPROVEMENT AND OPTIMIZATION OF PLANT PHENOTYPES" co-filed on Nov. 9, 1999 by Stemmer and Subramanian. Shuffled ADGPP genes and shuffled PEPC genes are optionally co-expressed in a cell or organism such as a plant to increase starch production and carbon fixation. Of course, shuffled Rubisco, ADPGPP, and PEPC can all be expressed together in a cell or organism such as a plant to increase carbon fixation, starch production, and the like.

In a further aspect, the present invention provides for the use of any apparatus, apparatus component, composition or kit herein, for the practice of any method or assay herein, and/or for the use of any apparatus or kit to practice any assay or method herein.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

All publications and patent applications herein are incorporated by reference to the same extent as if each individual publication or patent application was specifically and individually indicated to be incorporated by reference.

What is claimed is:

1. A method for obtaining an isolated polynucleotide encoding an ADPGPP enzyme having an ADPGPP catalytic activity that is significantly altered compared to an ADPGPP enzyme encoded by a parental polynucleotide, the method comprising:

recombining the sequences of a plurality of parental polynucleotide species encoding at least one ADPGPP enzyme under conditions suitable for sequence shuffling to form a resultant library of sequence-shuffled ADPGPP polynucleotides;

transferring said library into a plurality of plant host cells, thereby forming a library of transformants wherein sequence-shuffled ADPGPP polynucleotides are expressed;

assaying individual or pooled transformants for ADPGPP catalytic activity;

isolating at least one transformant that expresses a ADPGPP enzyme with a catalytic activity that is significantly altered compared to the activity of any enzyme encoded by the parental polynucleotide species; and recovering the sequence-shuffled ADPGPP polynucleotide from at least one isolated transformant identified as expressing an ADPGPP enzyme with a catalytic activity that is significantly altered compared to the activity of enzymes encoded by the parental polynucleotide species.

2. The method of claim 1, further comprising the step of subjecting a recovered sequence-shuffled ADPGPP polynucleotide encoding an ADPGPP enzyme having an ADPGPP catalytic activity that is significantly altered compared to an ADPGPP enzyme encoded by a parental polynucleotide to at least one subsequent round of recursive shuffling and selection, wherein said recovered sequence-shuffled ADPGPP polynucleotide is used as at least one parental polynucleotide species for subsequent shuffling.

3. The method of claim 1, wherein individual or pooled transformants are assayed for ADPGPP catalytic activity to determine the relative or absolute Km for a substrate, thereby identifying at least one transformant that expresses an ADPGPP enzyme with a significantly lower Km for the substrate than any ADPGPP enzyme encoded by the parental polynucleotide species.

4. The method of claim 1, wherein individual or pooled transformants are assayed for ADPGPP catalytic activity to determine the relative or absolute Km for an inhibitor, thereby identifying at least one transformant that expresses an ADPGPP enzyme with a significantly higher Km for inhibitor than any ADPGPP enzyme encoded by the parental polynucleotide species.

5. The method of claim 1, wherein individual or pooled transformants are assayed for ADPGPP catalytic activity to determine the relative or absolute Km for an activator, thereby identifying at least one transformant that expresses an ADPGPP enzyme with a significantly higher Km for activator than any ADPGPP enzyme encoded by the parental polynucleotide species.

6. The method of claim 1, wherein samples of individual transformants and their clonal progeny are isolated into discrete reaction vessels and assayed for ADPGPP activity.

7. The method of claim 1, wherein the step of recombining the sequences of the plurality of parental polynucleotide species is performed in vitro.

8. The method of claim 1, wherein at least one transformant is isolated that expresses an ADPGPP enzyme with a substrate specificity that is significantly altered compared to the activity of enzymes encoded by the parental polynucleotide species, and wherein the sequence-shuffled ADPGPP polynucleotide is recovered from at least one isolated transformant identified as expressing an ADPGPP enzyme with a substrate specificity that is significantly altered compared to the activity of enzymes encoded by the parental polynucleotide species.

9. A method for obtaining an isolated polynucleotide encoding an ADPGPP enzyme having increased catalytic activity with respect to a substrate, wherein said substrate is a molecule other than ATP or α-glucose-1-phosphate, the method comprising:

recombining the sequences of a plurality of parental polynucleotide species encoding at least one ADPGPP enzyme under conditions suitable for sequence shuffling to form a resultant library of sequence-shuffled ADPGPP polynucleotides;

transferring said library into a plurality of host cells, thereby forming a library of transformants wherein sequence-shuffled ADPGPP polynucleotides are expressed;

assaying individual or pooled transformants for ADPGPP catalytic activity with respect to said substrate;

isolating at least one transformant that expresses an ADPGPP enzyme having increased catalytic activity with respect to said substrate compared to any enzyme encoded by the parental polynucleotide species; and recovering the sequence-shuffled ADPGPP polynucleotide from at least one isolated transformant identified as expressing an ADPGPP enzyme having increased catalytic activity with respect to said substrate enzymes encoded by the parental polynucleotide species.

10. The method of claim 9, further comprising the step of subjecting a recovered sequence-shuffled ADPGPP polynucleotide encoding an ADPGPP enzyme having increased catalytic activity with respect to said substrate compared to the enzymes encoded by the parental polynucleotide species to at least one subsequent round of recursive shuffling and selection, wherein said recovered sequence-shuffled ADPGPP polynucleotide is used as at least one parental polynucleotide species for subsequent shuffling.

11. The method of claim 9, wherein samples of individual transformants and their clonal progeny are isolated into discrete reaction vessels and assayed for ADPGPP activity.

12. The method of claim 9, wherein the step of recombining the sequences of the plurality of parental polynucleotide species is performed in vitro.

13. The method of claim 9, wherein the host cells are plant cells.

14. The method of claim 1, wherein the recovered sequence-shuffled ADPGPP polynucleotide is introduced into a plant cell.

15. The method of claim 14, wherein the plant cell is regenerated to form a plant.

16. The method of claim 9, wherein the recovered sequence-shuffled ADPGPP polynucleotide is introduced into a plant cell.

17. The method of claim 16, wherein the plant cell is regenerated to form a plant.

* * * * *